US012673069B2

(12) United States Patent
Kornhaber et al.

(10) Patent No.: US 12,673,069 B2
(45) Date of Patent: Jul. 7, 2026

(54) INTRA-ARTICULAR NEEDLE PLACEMENT DEVICE AND METHOD OF USING

(71) Applicant: Avanos Medical Sales, LLC, Alpharetta, GA (US)

(72) Inventors: Gregory J. Kornhaber, Flemington, NJ (US); David Toledo-Velasquez, Doylestown, PA (US)

(73) Assignee: Avanos Medical Sales, LLC, Alpharetta, GA (US)

( * ) Notice: Subject to any disclaimer, the term of this patent is extended or adjusted under 35 U.S.C. 154(b) by 1058 days.

(21) Appl. No.: 17/841,268

(22) Filed: Jun. 15, 2022

(65) Prior Publication Data

US 2023/0019674 A1     Jan. 19, 2023

Related U.S. Application Data

(63) Continuation of application No. 17/840,300, filed on Jun. 14, 2022, now Pat. No. 11,690,868, which is a (Continued)

(51) Int. Cl.
*A61M 5/46*          (2006.01)
*A61K 31/728*          (2006.01)
(Continued)

(52) U.S. Cl.
CPC ............ *A61K 31/728* (2013.01); *A61K 35/19* (2013.01); *A61M 5/34* (2013.01); *A61M 5/345* (2013.01);
(Continued)

(58) Field of Classification Search
CPC ...... A61M 5/345; A61M 5/427; A61M 5/486; A61M 2205/3344
See application file for complete search history.

(56) References Cited

U.S. PATENT DOCUMENTS 7,364,567 B2 *  4/2008  Beyerlein ............ A61B 5/4839
                                                 604/117
8,608,665 B2 *  12/2013  Vad ................... A61B 17/3401
                                                 600/587

(Continued)

FOREIGN PATENT DOCUMENTS

WO          2019210140 A1    10/2019

OTHER PUBLICATIONS

Evaluation Engineering, "Understanding Real Time for Measurement and Automation", 1999, ElectronicDesign, Nelson Publishing Inc., 9 pages, available online at https://www.electronicdesign.com/home/article/21200297/understanding-real-time-for-measurement-and-automation. (Year: 1999).

(Continued)

*Primary Examiner* — Nathan R Price
(74) *Attorney, Agent, or Firm* — Meunier Carlin & Curfman LLC

(57)          ABSTRACT

The present invention relates to a device for measuring, recording, and acting in response to changes in air pressures encountered through the lumen of a connected needle. The device signals when it has been powered and signals when the device recognizes both pressures and pressure change rates indicative of synovial cavity joint penetration, such as knee joint penetration. Synovial cavity pressures detected and acted upon may either be supra- (positive) or sub-atmospheric (negative). Internal light emitting diodes and a laptop connected display are demonstrated as signaling and communication mechanisms. Methods for delivering medicaments into human and animal intra-articular cavities or joints such as synovial cavities are provided. Furthermore, methods for facilitating the diagnoses of joint effusion also are provided.

10 Claims, 19 Drawing Sheets

Figure 1:
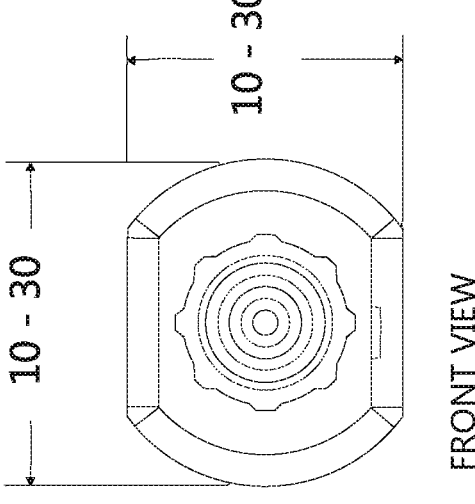
Figure 1:
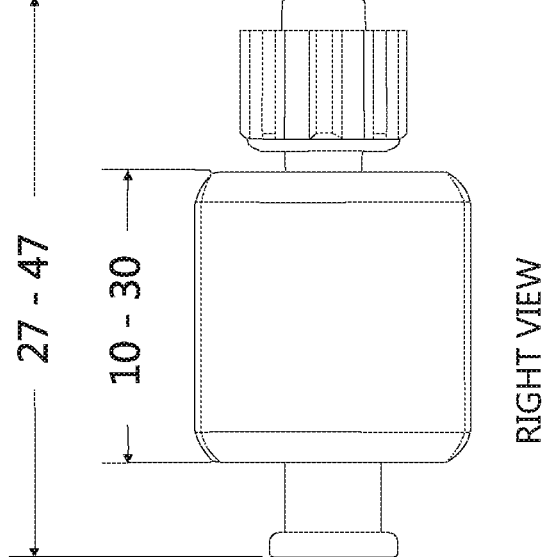

Related U.S. Application Data continuation-in-part of application No. PCT/US2020/064855, filed on Dec. 14, 2020.

(60) Provisional application No. 62/949,885, filed on Dec. 18, 2019.

(51) Int. Cl.

| | |
|---|---|
| *A61K 35/19* | (2015.01) |
| *A61M 5/34* | (2006.01) |
| *A61M 5/42* | (2006.01) |
| *A61M 5/48* | (2006.01) |
| *A61P 19/02* | (2006.01) |
| *A61B 5/03* | (2006.01) |
| *A61K 35/28* | (2015.01) |
| *A61M 5/14* | (2006.01) |

(52) U.S. Cl.
CPC .............. *A61M 5/427* (2013.01); *A61M 5/46* (2013.01); *A61M 5/486* (2013.01); *A61P 19/02* (2018.01); *A61B 5/03* (2013.01); *A61K 35/28* (2013.01); *A61M 5/14* (2013.01); *A61M 2205/3344* (2013.01); *A61M 2205/52* (2013.01); *A61M 2205/702* (2013.01); *A61M 2210/08* (2013.01); *A61M 2210/086* (2013.01); *A61M 2250/00* (2013.01)

(56) References Cited

U.S. PATENT DOCUMENTS

| | | | |
|---|---|---|---|
| 12,397,134 B2 * | 8/2025 | Hulvershorn | ......... A61M 25/06 |
| 2003/0154056 A1 | 8/2003 | Ito et al. | |
| 2009/0326411 A1 | 12/2009 | Eide | |
| 2010/0069851 A1 | 3/2010 | Vad et al. | |
| 2011/0054353 A1 | 3/2011 | Hulvershorn et al. | |
| 2011/0202012 A1 | 8/2011 | Bartlett | |
| 2011/0270027 A1 | 11/2011 | Augarten et al. | |
| 2011/0298628 A1 | 12/2011 | Vad et al. | |
| 2012/0330184 A1 | 12/2012 | Mahapatra et al. | |
| 2016/0113576 A1 | 4/2016 | Hulvershorn et al. | |
| 2016/0374612 A9 | 12/2016 | Hulvershorn et al. | |
| 2017/0290546 A1 | 10/2017 | Antonio et al. | |
| 2019/0167169 A1 | 6/2019 | Bohm et al. | |
| 2021/0236737 A1 * | 8/2021 | Ritchie | .............. A61B 17/3401 |

OTHER PUBLICATIONS

The International Search Report and Written Opinion, dated Apr. 13, 2021, in the related PCT Appl. No PCT/US20/64855.

The extended European search report, dated Nov. 10, 2022, in the related European Appl. No. 22179748.3.

The extended European search report, mailed on Mar. 11, 2024, in related European Appl. No. 20901272.3.

Office Action received in corresponding Canadian Application No. 3174282 mailed May 15, 2024.

* cited by examiner

FRONT VIEW

RIGHT VIEW (1) Pass ambient threshold (-1 mmHg)? YES (2) Pass slope threshold over a sliding 250 ms window (1 mmHg/sec)? YES (3) Pass stability check over a sliding 250 ms window starting after passing the slope threshold? NO (1) Did we pass the ambient threshold (-1 mmHg)? YES (2) Pass slope threshold over a sliding 250 ms window (1 mmHg/sec)? YES (3) Did we pass the stability check over a sliding 250 ms window starting after passing the slope threshold? YES (4) Green LED activated (5) Green LED activation lock because pressure remained beyond ambient threshold for at least 2 seconds.

(1) Pass ambient threshold (-1 mmHg)? YES (2) Pass slope threshold over a sliding 250 ms window (1 mmHg/sec)? YES (3) Pass slope threshold over a sliding 250 ms window? YES (4) Green LED activated (5) Green LED deactivated because pressure did not remain beyond ambient threshold for at least 2 seconds.

INTRA-ARTICULAR NEEDLE PLACEMENT DEVICE AND METHOD OF USING

CROSS-REFERENCE TO RELATED APPLICATIONS

This application is a Continuation, which claims the benefit from Continuation-In-Part application Ser. No. 17/840,300, filed Jun. 14, 2022, which claims the benefit from PCT/US20/64855, filed Dec. 14, 2020, which claims priority from Provisional Application No. 62/949,885, filed on Dec. 18, 2019, which are all hereby incorporated by reference in all of their entireties.

BACKGROUND OF THE INVENTION

A significant number of therapeutic intra-articular injections, in particular synovial cavity knee injections, are incorrectly placed outside the joint (Berkoff et al., 2012; Douglas, 2014; Hermans et al., 2011; Telikicherla and Kamath, 2016). Not surprisingly correct intra-articular or synovial cavity needle placement is correlated with greater efficacy (Finnoff et al., 2015, 2015; Jones et al., 1993; Lundstrom et al., 2020; Sibbitt et al., 2009). Despite the benefits of accurately placed intra-articular joint injections, such as knee injections, insurers do not consider injection guidance technologies, i.e. ultrasound and fluoroscopy, medically necessary for most patients receiving intra-articular injections. Consequently, few such guidance technologies and devices are in regular use for intra-articular injections of the knee. A second impediment to using ultrasound and fluoroscopy is staff training and equipment costs. Presently, there is a need for a device that can confirm proper intra-articular needle placement that is safe, effective, inexpensive, and intuitive with minimal instruction prior to use. Further, such device should be small and unobtrusive, and importantly, capable of seamless integration with current practices.

One such device is disclosed in U.S. Pat. No. 8,608,665, wherein a method of using a pressure detection device for confirming intra-articular needle placements is found. The method exploits a physiologic property of the intra-articular cavity that is not shared by surrounding tissues, the sub-atmospheric condition (negative pressure) of the intra-articular space in non-effused knees. Intra-articular pressures are thought to play a role in condylar cartilage nutrition, meniscal load bearing, and joint stability (Irvin, 2015). U.S. Pat. No. 8,608,665 describes an algorithm dependent on detection of atmospheric pressure and the pressure within the intra-articular space of the knee. Specifically, the algorithm indicates joint penetration if the difference in atmospheric and needle-sensed pressure is (i) beyond a defined negative threshold, (ii) sustained beyond a negative threshold for a defined period, and (iii) where the change in pressure over time is significantly steep and negative in its slope (e.g. $\Delta P/\Delta T < -1.5$), and (iv) pressure stabilization is set within a dynamically-calculated variability tolerance over a defined time.

Literature suggests that the method described by U.S. Pat. No. 8,608,665 may fail to detect the intra-articular cavity for a large fraction of osteoarthritis (OA) patients presenting knee pain. For instance, (1) a report suggests that >90% of OA patients presenting knee pain and x-ray diagnosed OA also have effusions (Hill et al., 2001); (2) effusions are correlated with a supra-atmospheric intra-articular condition (positive pressure); and (3) effusions are often underdiagnosed, i.e. weak kappa scores reported for intra and interobserver clinical diagnoses of knee OA effusion (Hauzeur et al., 1999; Maricar et al., 2016). Accordingly, a device with an algorithm solely dependent on the sensing of the sub-atmospheric condition of the intra-articular space lacks adequate sensitivity for the population to whom it was intended to serve. Secondly, it is not widely recognized that not all positively pressured joints are effused. Positive pressure can also occur in response to flexion, application of pressure proximal but external to the joint, and load-bearing (such as standing). The methods of U.S. Pat. No. 8,608,665 would not detect these positively pressured joints either.

A joint effusion is the abnormal accumulation of fluid in or around a joint and is commonly caused by infection, injury, and arthritis. Excess joint fluid volume decreases range of motion (Strand et al., 1998; Wood et al., 1988) and increases intra-articular pressures (Caughey and Bywaters, 1963). Elevated intra-articular pressures in turn, correlate with increased pain (Goddard and Gosling, 1988).

While a viscosupplement injection is intended to treat knee osteoarthritis (OA) pain in patients who have failed to respond adequately to conservative nonpharmaco logic therapy and simple analgesics (e.g., acetaminophen), the injection itself could cause additional pain if that injection is performed on an effused knee (by adding fluid to a joint that already has an abnormally high fluid level). Consequently, viscosupplement prescribing guidelines state that effusions should be removed prior to viscosupplement injection. As stated previously, knee effusions commonly go undiagnosed during standard clinical examination (Hauzeur et al., 1999; Kane et al., 2003; Maricar et al., 2016). It would be advantageous to know prior to administering an intra-articular viscosupplement injection as to the effusion status of a targeted joint.

In response to the previously highlighted short comings, the present invention revises the pressures sensing method and reconfigures the device to be responsive to both sub-atmospheric and supra-atmospheric intra-articular conditions. Specifically, an algorithm is constructed (see EXAMPLE 5) such that joint penetration is indicated if the difference in atmospheric and needle-sensed pressure is (i) beyond a defined negative or positive threshold; (ii) sustained beyond a threshold for a defined period; and (iii) where the change in pressure over time is significantly steep and either positive or negative in its slope. A further fourth criterion to the algorithm method is exemplified in Example 8. The signal for joint penetration is only provided if pressures satisfy set defined conditions, and (iv) stabilization is set within a dynamically-calculated threshold over a defined time.

Misplaced intra-articular knee injections are common and are less efficacious than correctly placed intra-articular injections. Ultrasound and fluoroscopy are two joint injection guidance technologies that improve accuracy. As indicated above, many payors do not consider these solutions medically necessary. The cost of utilization, which is non-trivial, represents a barrier to many patients. Another barrier is high acquisition costs and training prior to implementation. Consequently, there is an opportunity for a low-cost solution requiring minimal training. Ideally the solution should be capable of integration with current practices.

The present invention describes a device and methods for confirming synovial cavity needle placement and for identifying joint effusion. The device exploits discernable differences in pressure between extra-articular issues and synovial cavities. These differences inform the clinician the moment the device connected needle penetrates the synovial cavity. The present invention represents an improvement over previous joint penetration confirmation by pressure detection technology in that both positive and negative pressures are acted upon to inform the user of synovial cavity needle placement prior to administering a medicament to the subject. And if positive pressures are indicative of an effusion, the clinician could take appropriate action prior to administering a medicament.

Further, it is pointed out that the device and methods of the present invention also are useful for veterinary procedures on such animals as horses, dogs, cats, cows, goats, and sheep, as well as in human subjects.

The design and construction of a laptop connected device and a standalone self-powered device are provided. Also provided are bench-top simulated joint, cadaveric knee joint, and live animal synovial joint studies utilizing the laptop connected device.

SUMMARY OF THE INVENTION

The present invention relates to a device for detecting pressure differences encountered during a synovial cavity injection. Synovial cavities exhibit a differential pressure reading at a normal steady state. Additionally, said differential pressure may be manifested by a diseased state in a subject, or that pressure differential may have been induced by force or manipulation.

The device of the invention comprise a power source (Panasonic CR1220 3V battery), custom stamped battery retainer, a power source isolation mechanism (non-conductive pull tab), a microprocessor (ST Microelectronics; part number STM8L101), two LEDs (Everlight Electronics), where one LED is blue (part number EAST 16084BB0) for indicating device "on" and the other LED is green (part number EAST0603GA0) for indicating joint cavity penetration, necessary capacitors and resistors, male and female luer locks to ISO 594 and ISO 80369-7 specification, a hollow tube connecting male and female luer locks, within which is mounted a pressure transducer (Bosch BMP280 absolute barometric piezoresistive pressure sensor or TDK ICP-10111 Pressure Transducer (when this transducer is used, linear voltage regulators also are useful.) The device is housed within a small plastic housing constructed of medical grade plastic with known biocompatibility characteristics and sterility process compatibilities. Measured absolute pressures are stored and analyzed by the microprocessor. Here supra (positive) or sub-atmosphere (negative) pressure differentials and rates of change in pressure over time are calculated, and an algorithm is executed to determine if the pressure differentials and rates of change in pressure over time is indicative of synovial cavity penetration.

The device further comprises one or more light emitting diodes of different colors that illuminate when a needle that is connected to the device is exposed to a synovial cavity such as that found within the intra-articular space of the knee. Human anatomical examples of synovial joints include: neck vertebrate (pivot joint); ankle, elbow, and knee joints (hinge joints); trapeziometacarpal "thumb" joint (saddle joints); carpal, metacarpal, tarsal, metatarsal, and zygapophysial "facet" vertebral joints (plane joints); radio-carpal, metacarpophalangeal, and metatarsophalangeal joints (condyloid joints); and shoulder and hip joints (ball-and-socket joints).

The device of the present invention confirms synovial cavity needle placement for the purpose of delivering medicaments in both human being and animals. Further, the device of the present invention is useful in diagnosing joint effusion.

It is an object of the present invention to record either positive (supra-atmospheric) or negative (sub-atmospheric) pressure when using the device and methods of the present invention.

It is further an object of the invention to provide a method of using the device of the invention to provide needle placement confirmation for synovial cavity-related applications and record such resulting data in real time.

A further object of the invention is to optionally display such resulting data in real-time to either a peripherally connected device, e.g. a USB or WiFi connected to a secondary source computer such as a laptop, tablet cloud base or smartphone, or via the device itself.

The availability of low-cost components enable single-use configurations which (i) mitigate nosocomial infection risks associated with multi-use devices, and (ii) allow for lower transfer costs thereby facilitating greater adoption of the technology.

An additional object of the invention is a method for diagnosing joint effusion, such as intra-articular knee effusions. In one embodiment of the device the clinician is informed via one or more LEDs, or one or more LCDs, or by video output of pressure over time data to a connected laptop, as to the differential positive and negative pressures detected. It is then up to the clinician to decide the proper course of action, i.e. to drain the effusion if the device indicates positive pressure, or to proceed with the injection.

A further object of the invention is to provide methods for confirming correct synovial cavity needle placement and administering a medicament. The predetermined threshold positive pressure is greater than 0.5 mmHg. A range of 0.5 mmHg to about 200 mmHg is used. The predetermined threshold negative pressure is less than negative 0.5 mmHg. The range is negative 0.5 mmHg to negative 100 mmHg. The predefined time period is at least 100 ms. In one method, the slope of pressure change over time is positive and greater than 1 mmHg/second. In another method, the slope of change over time is negative and less than negative 1 mmHg/second. In an embodiment, the predefined time period is at least 250 msec.

It is an object of the present invention to provide methods to first establish a baseline atmospheric pressure and record a series of pressure readings at defined time intervals. Joint penetration is indicated if the difference between the reference atmospheric pressure and needle-sensed pressure is (i) beyond a defined negative or positive threshold; (ii) sustained beyond that threshold for a minimum defined period; (iii) where the change in pressure over corresponding change in time is equal to or exceeds a minimum slope criteria, and (iv) where the magnitude of change stabilizes to within a dynamically calculated variability tolerance. Note that the slope can be either positive or negative.

The methods of the present invention to administer a medicament require attaching a syringe and needle to the device and powering on the device prior to usage. Then the user monitors visual indicators displayed on the device during a synovial injection procedure. Upon observing the joint penetration signal, the user administers the medicament.

The methods of the invention that support effusion diagnoses involve the same method as above, accept that upon observing a warning signal indicative of excessive synovial joint pressure, appropriate medical action to relieve or further diagnose the effusion is undertaken.

DETAILED DESCRIPTION OF THE DRAWINGS

FIG. 1. Device dimensions (in millimeters).

Figure 2:
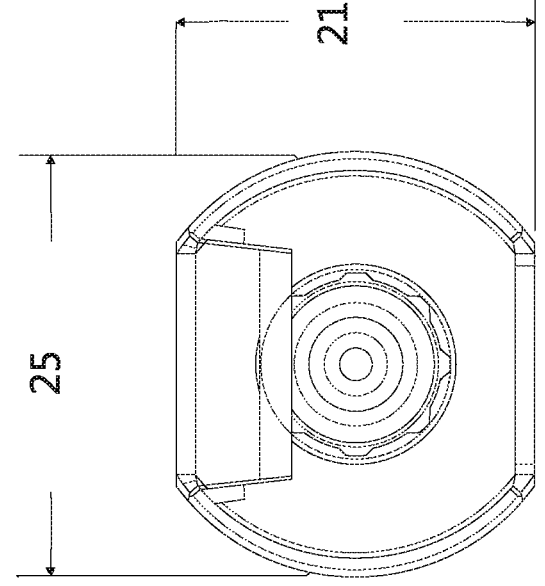
Figure 2:
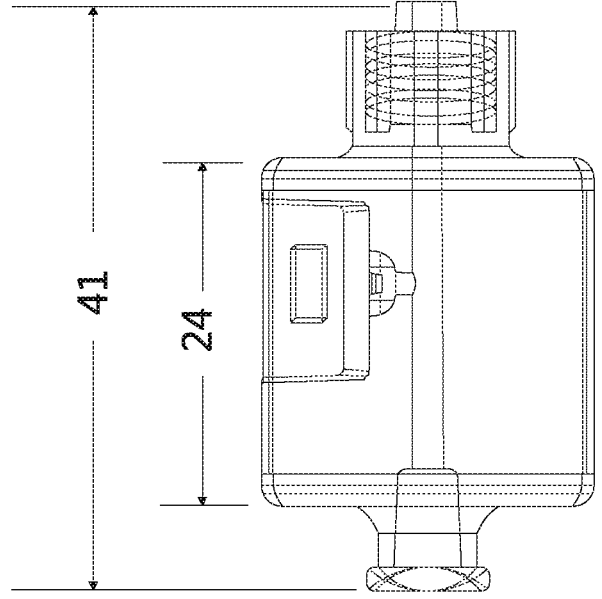

FIG. 2. Device dimensions (in millimeters) of the laptop connected device sensor housing: sideview (left panel) and 90° rotated about the vertical axis (right panel). Note the hollow tube connecting male and female leer locks, and the circuit board mounted piezoresistive pressure sensors positioned peripherally to the flow path.

Figure 3:
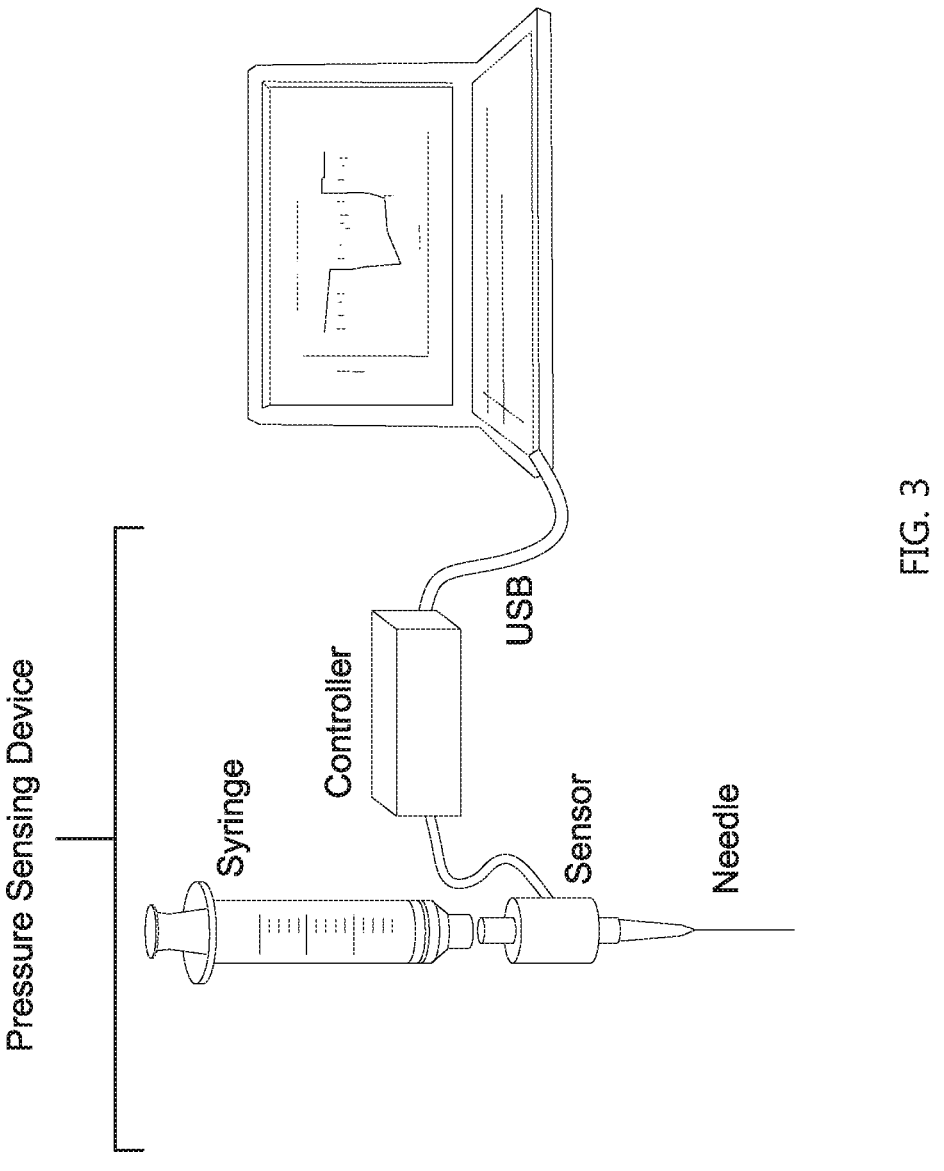

FIG. 3. Diagram of the laptop connected device, showing the sensor housing, syringe, needle, Arduino controller, and laptop running a custom data capture and visualization software application.

Figure 4:
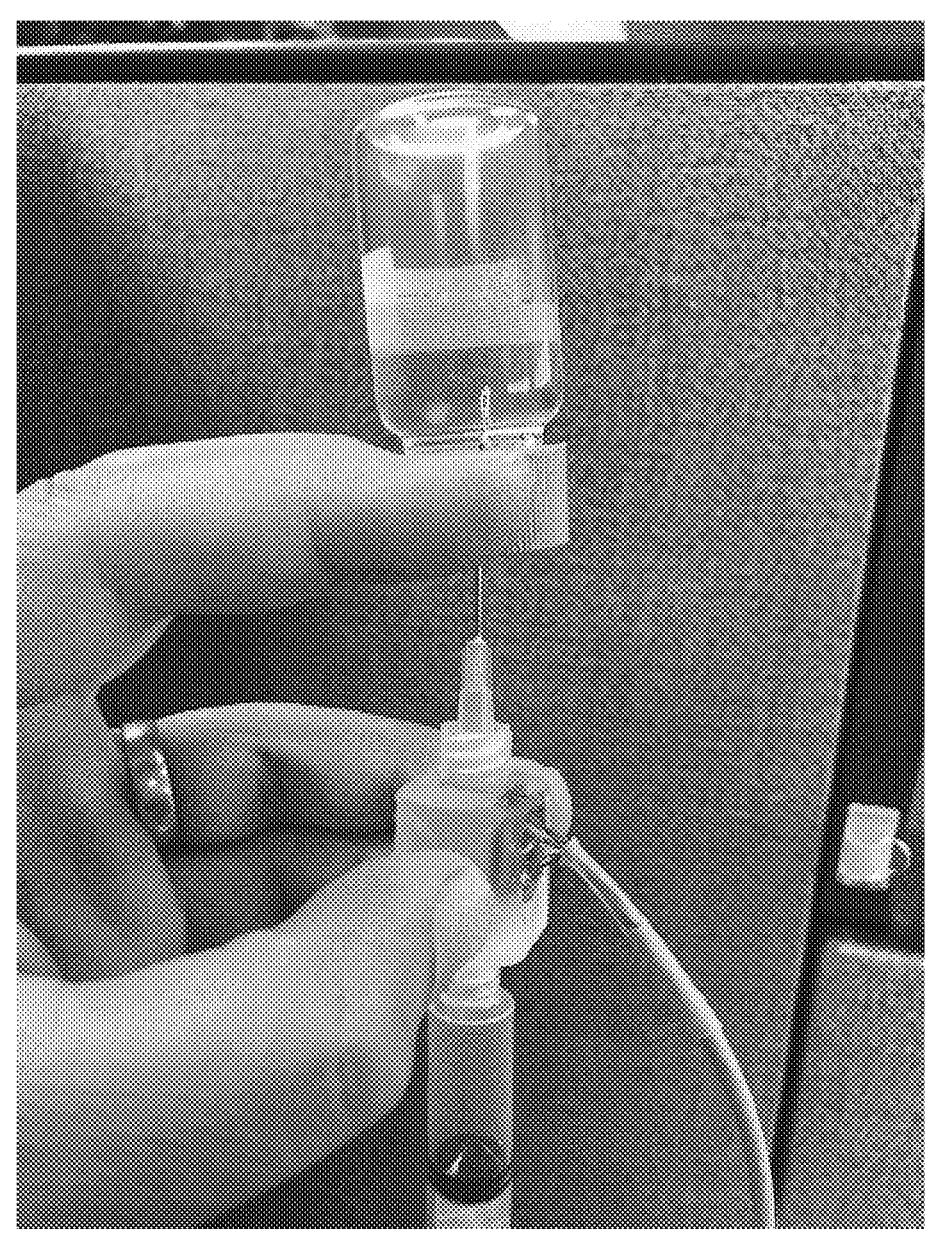

FIG. 4. Benchtop test device consisting of a partially liquid filled and pressurized vial. The vial incorporates an airtight cap with silicone septum for resealing the holes created by syringe needle punctures.

Figure 5:
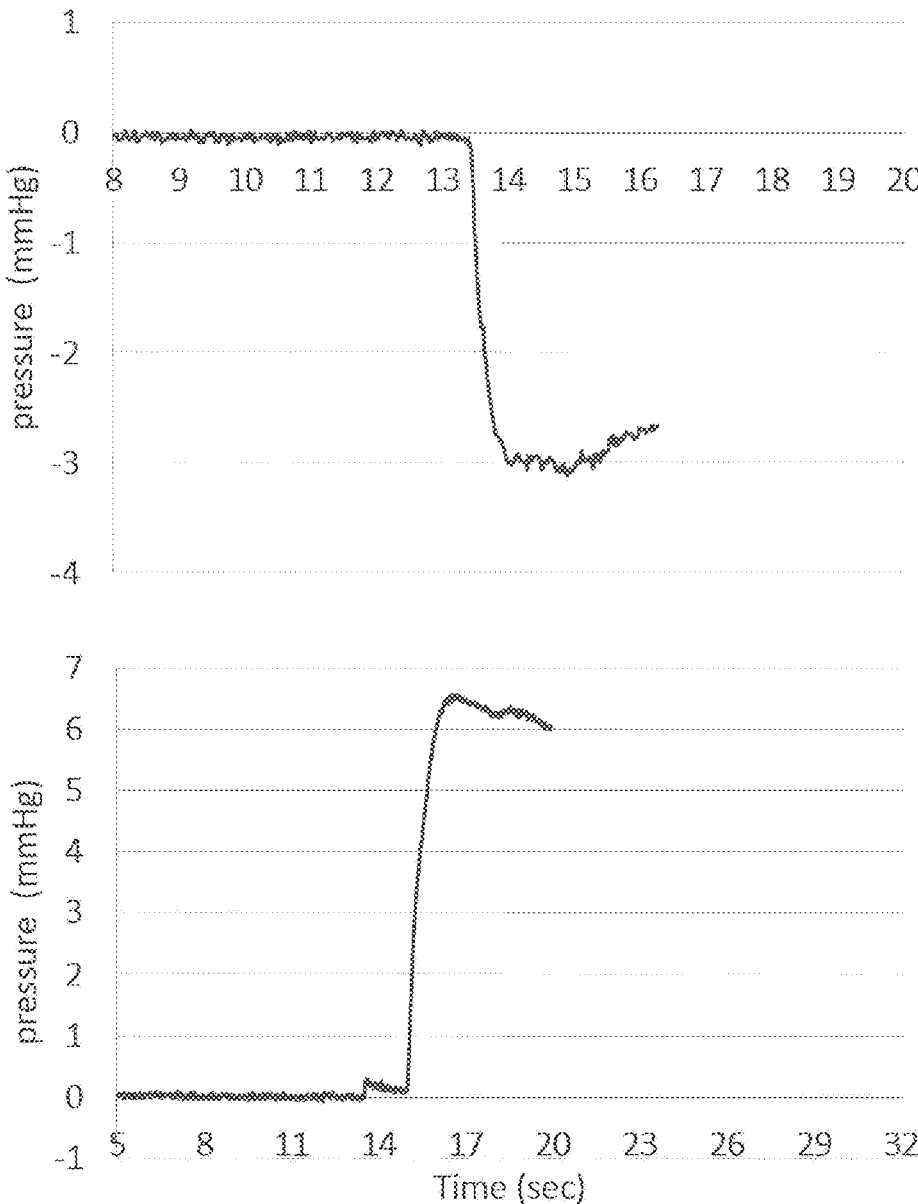

FIG. 5. Laptop connected device pressure over time data from inverted liquid filled/pressurized vial; vacuum conditioned vial (upper panel) and pressurized vial (lower panel).

Figure 6:
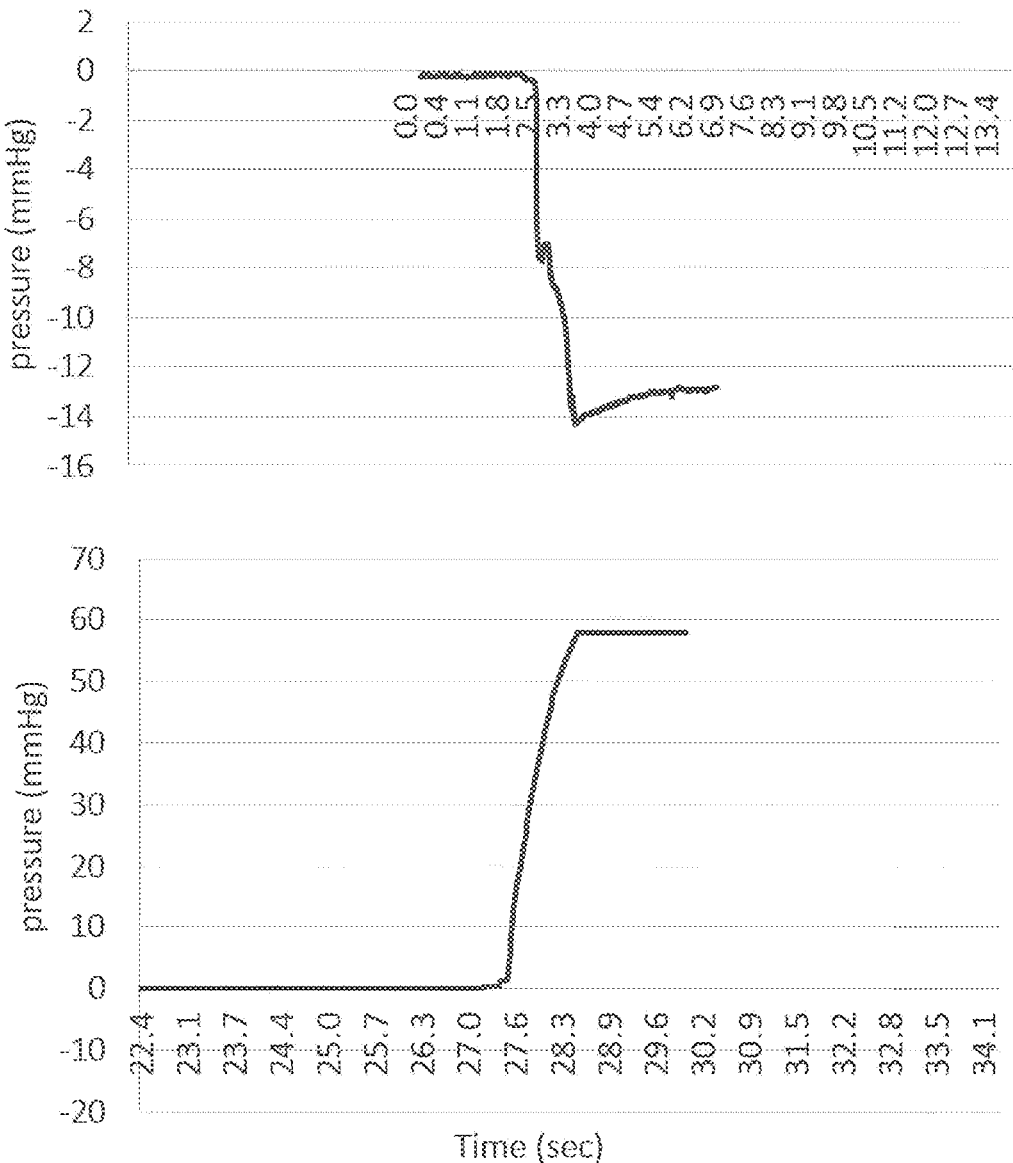

FIG. 6. Laptop connected device pressure over time data from equine stifle joint tap (upper panel) and equine fetlock joint tap (lower panel).

Figure 7:
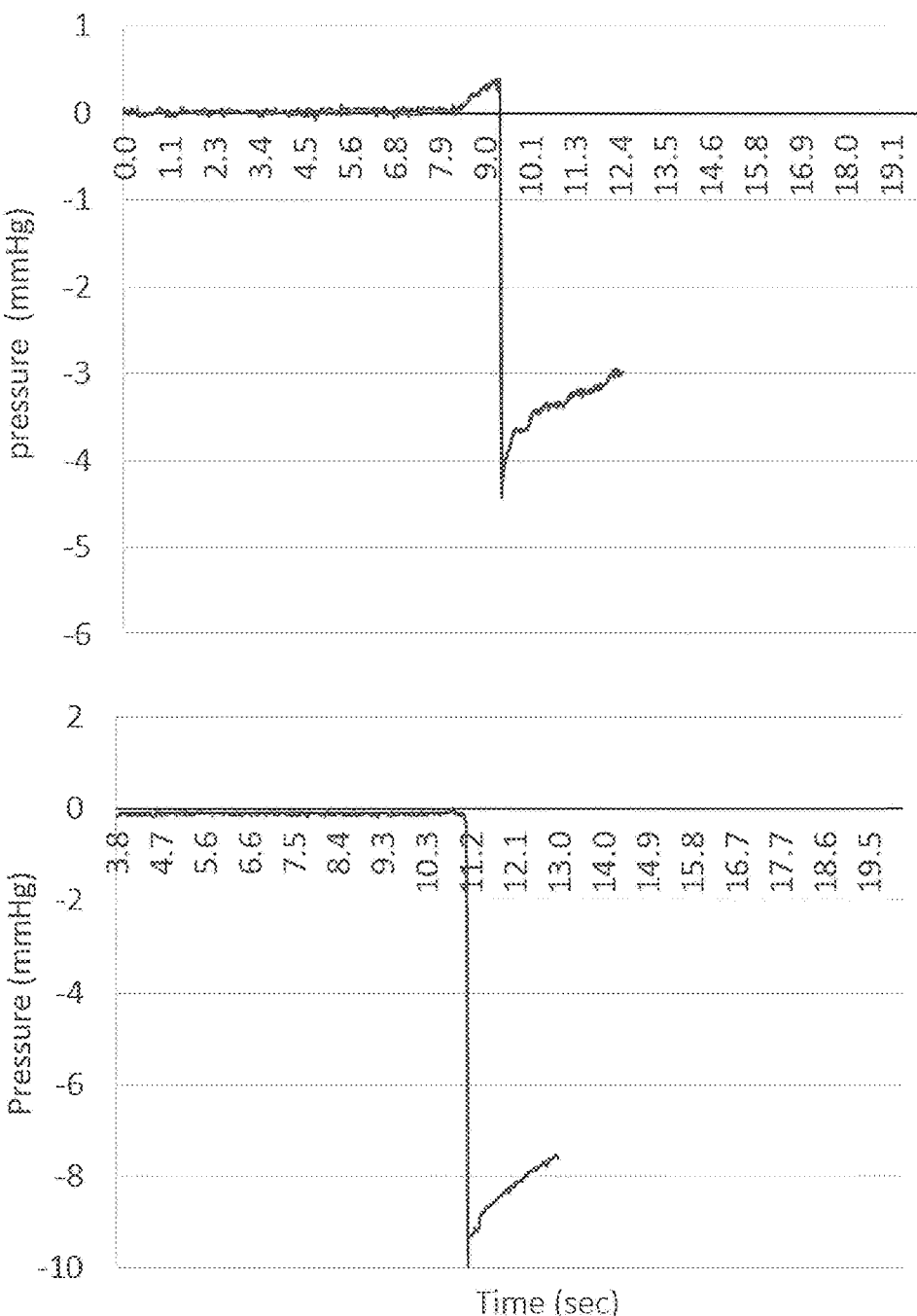

FIG. 7. Laptop connected device pressure over time data from goat carpal joint tap (upper panel) and goat stifle joint tap (lower panel).

Figure 8:
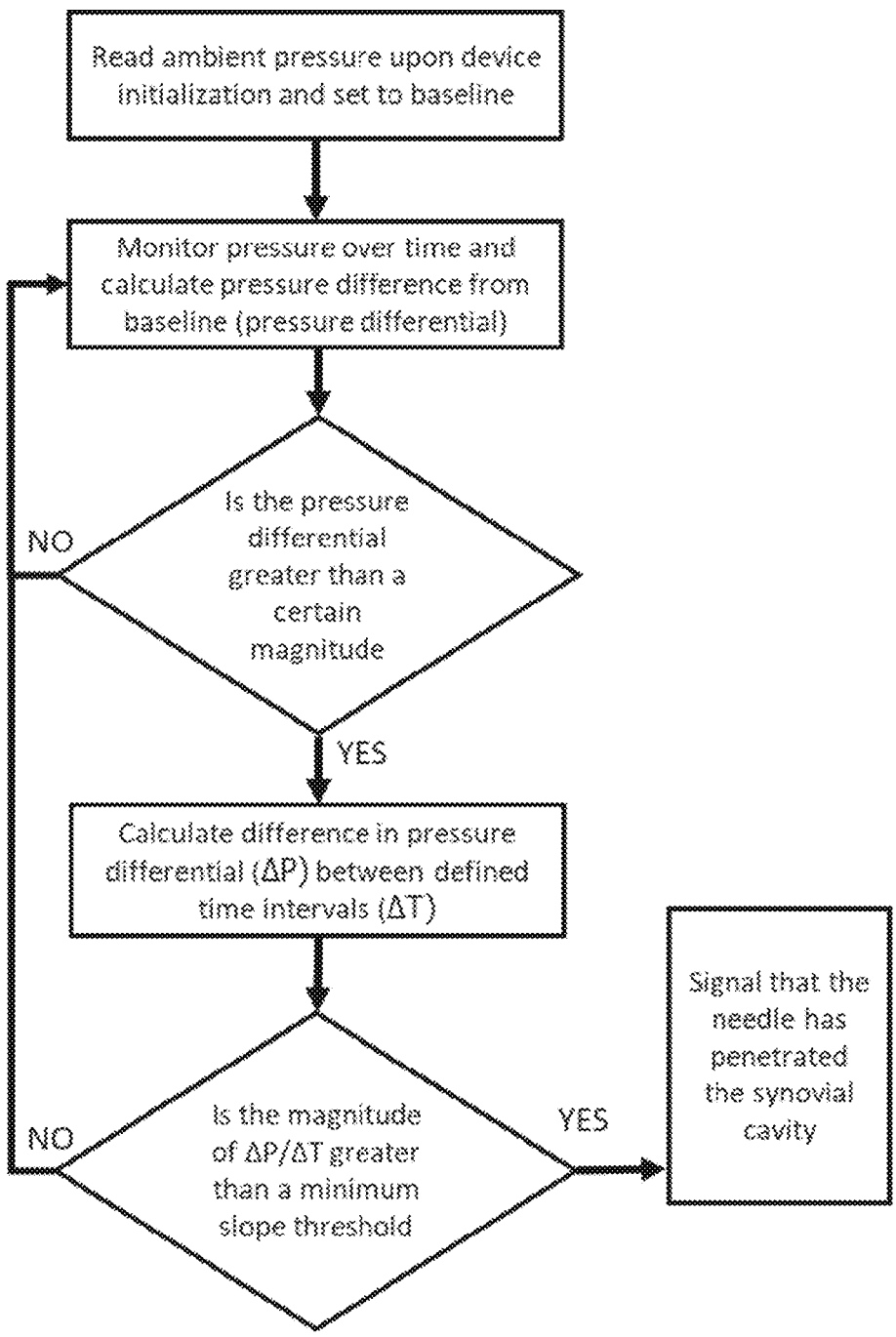

FIG. 8. Graphical representation of the alpha-algorithm method deployed in this invention.

Figure 9:
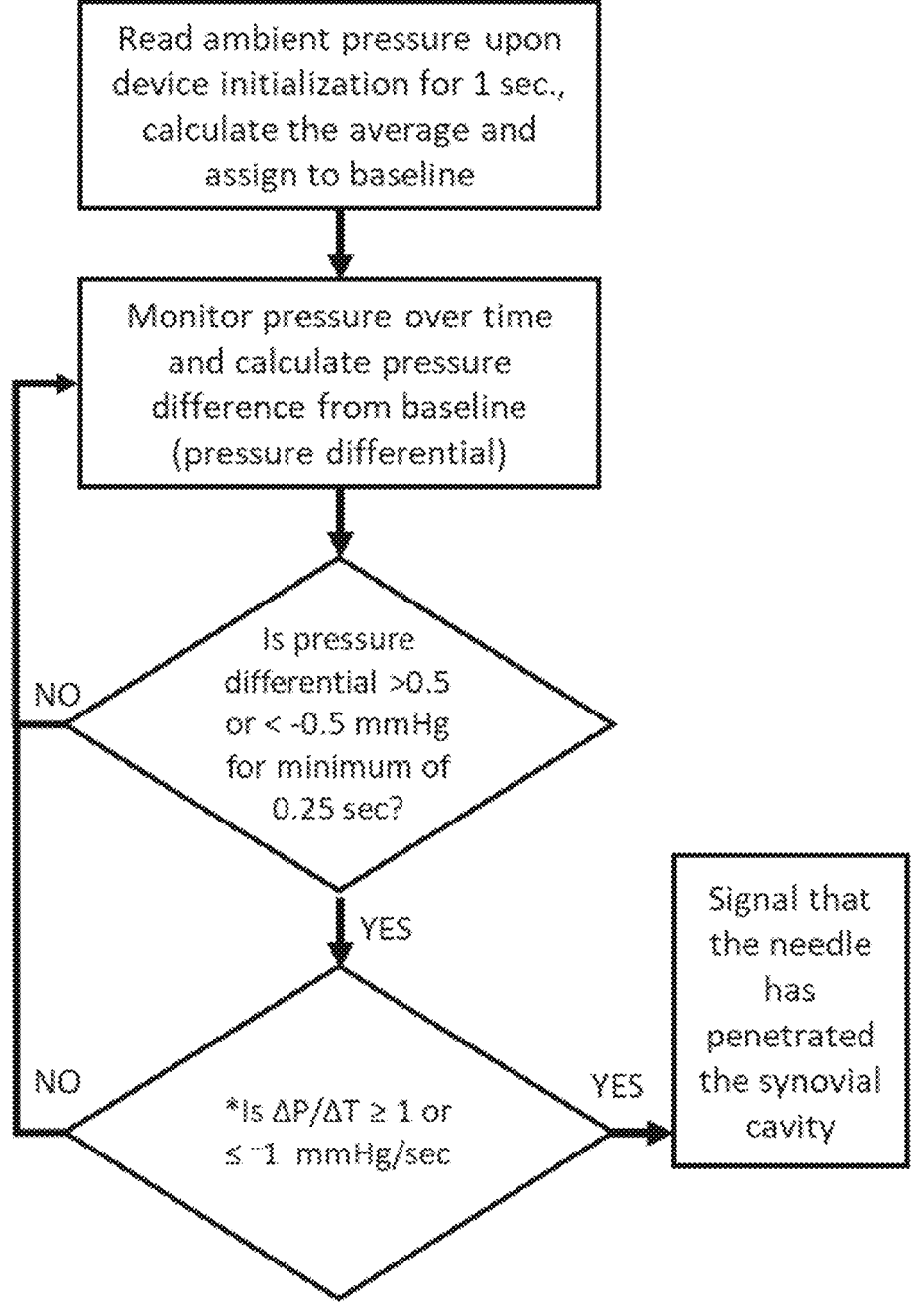

FIG. 9. Graphical representation of the alpha-algorithm method deployed in this invention, with the parameters specific to Example 5 defined. Note here $\Delta P$=the difference in pressure differentials at time t2 and time t1, where time t2=time t1+0.25 sec, and $\Delta T$=t2−t1 or 0.25 sec.

Figure 10:
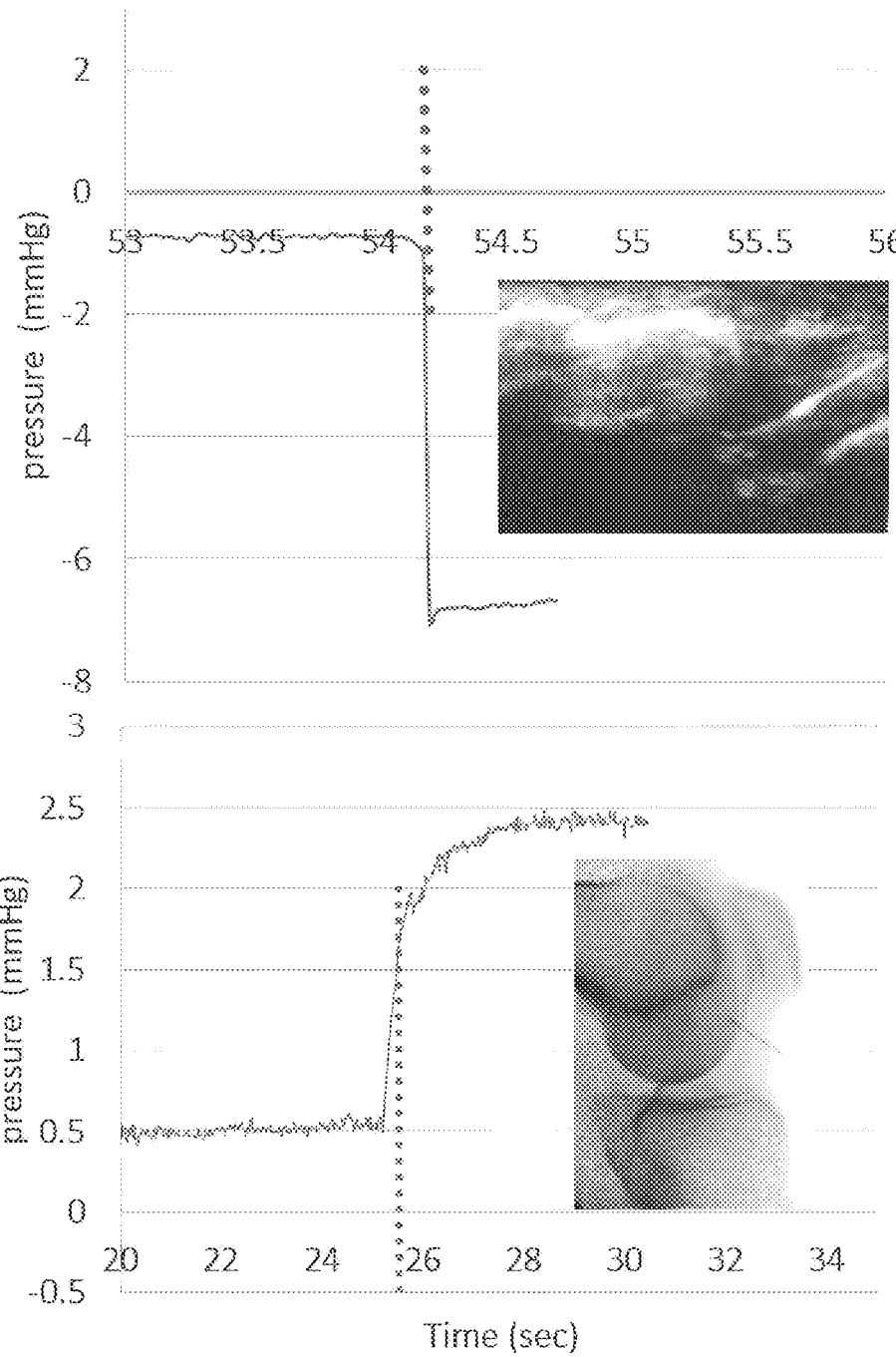

FIG. 10. Laptop connected device pressure over time data from ultrasound guided human lateral retropatellar joint tap (upper panel) and fluoroscopic guided human lateral parapatellar joint tap (lower panel). Also shown, the needle location by ultrasound (inset image, upper panel) and by fluoroscopy (inset image, lower panel). The dotted line indicates when the alpha-algorithm determined that the needle penetrated the intra-articular cavity.

Figure 11:
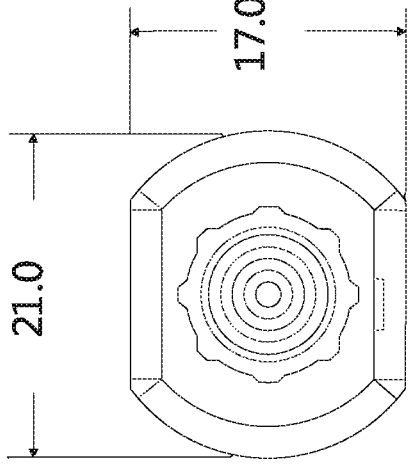
Figure 11:
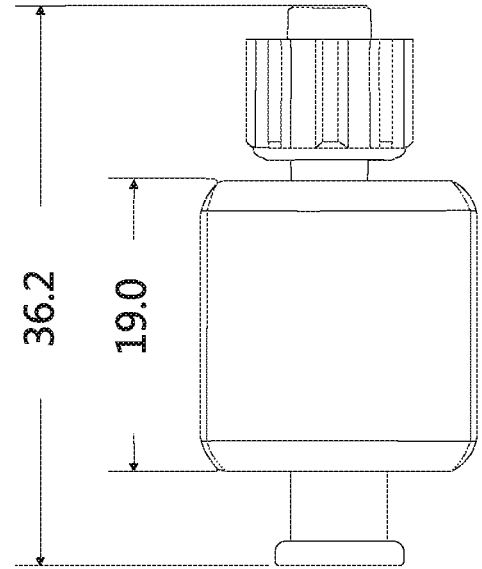

FIG. 11. Device dimensions (in millimeters) of the standalone device that is constructed and tested: side view (left panel) and 90° rotated about the vertical axis (right panel).

Figure 12:
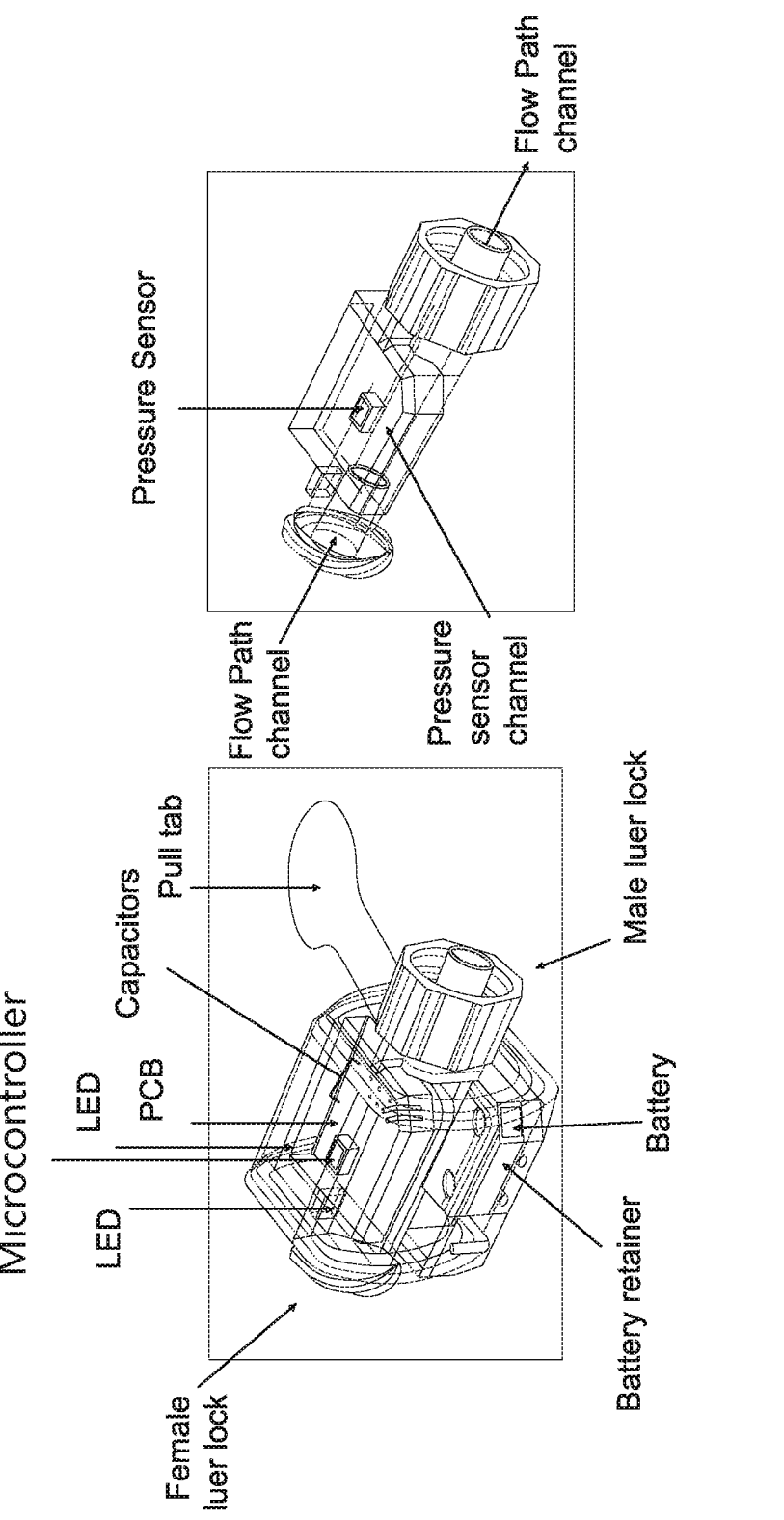

FIG. 12. Standalone alpha CAD drawings, with key components indicated.

Figure 13:
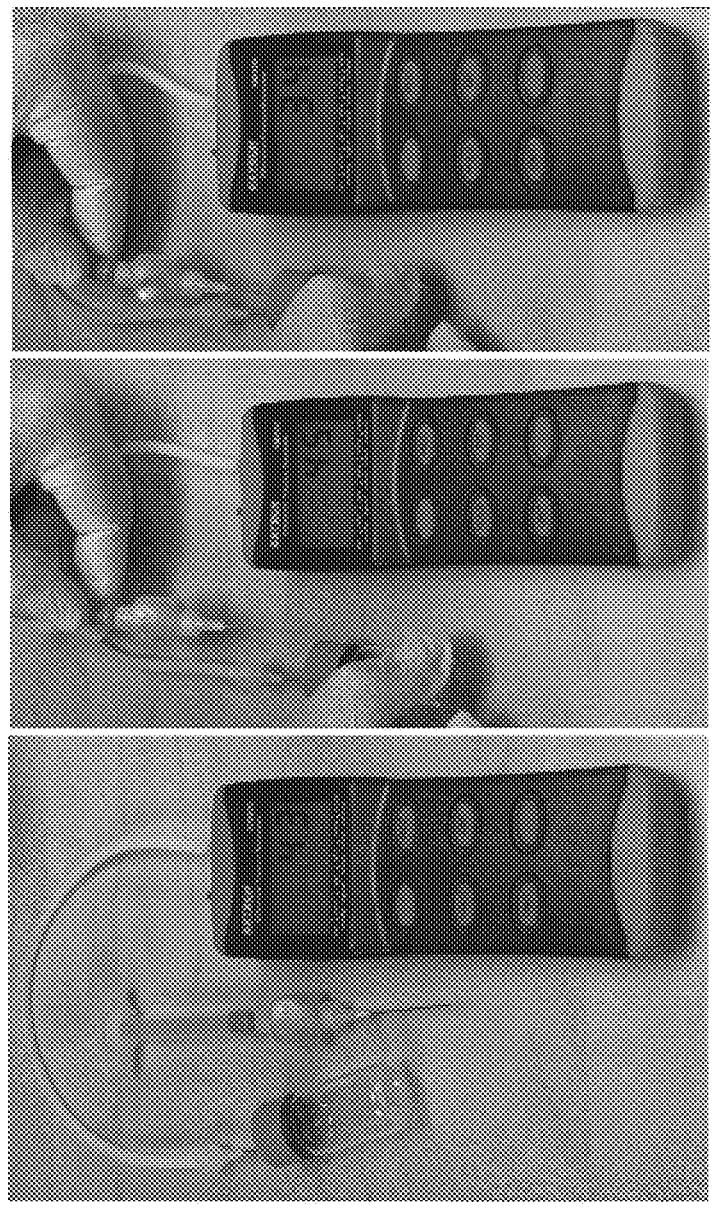

FIG. 13. Standalone alpha-prototype negative pressure detection illustration (approximately −4.3 mmHg reading on manometer). Note that the blue LED turned off and the green LED turned on upon sensing negative pressure within vial.

Figure 14:
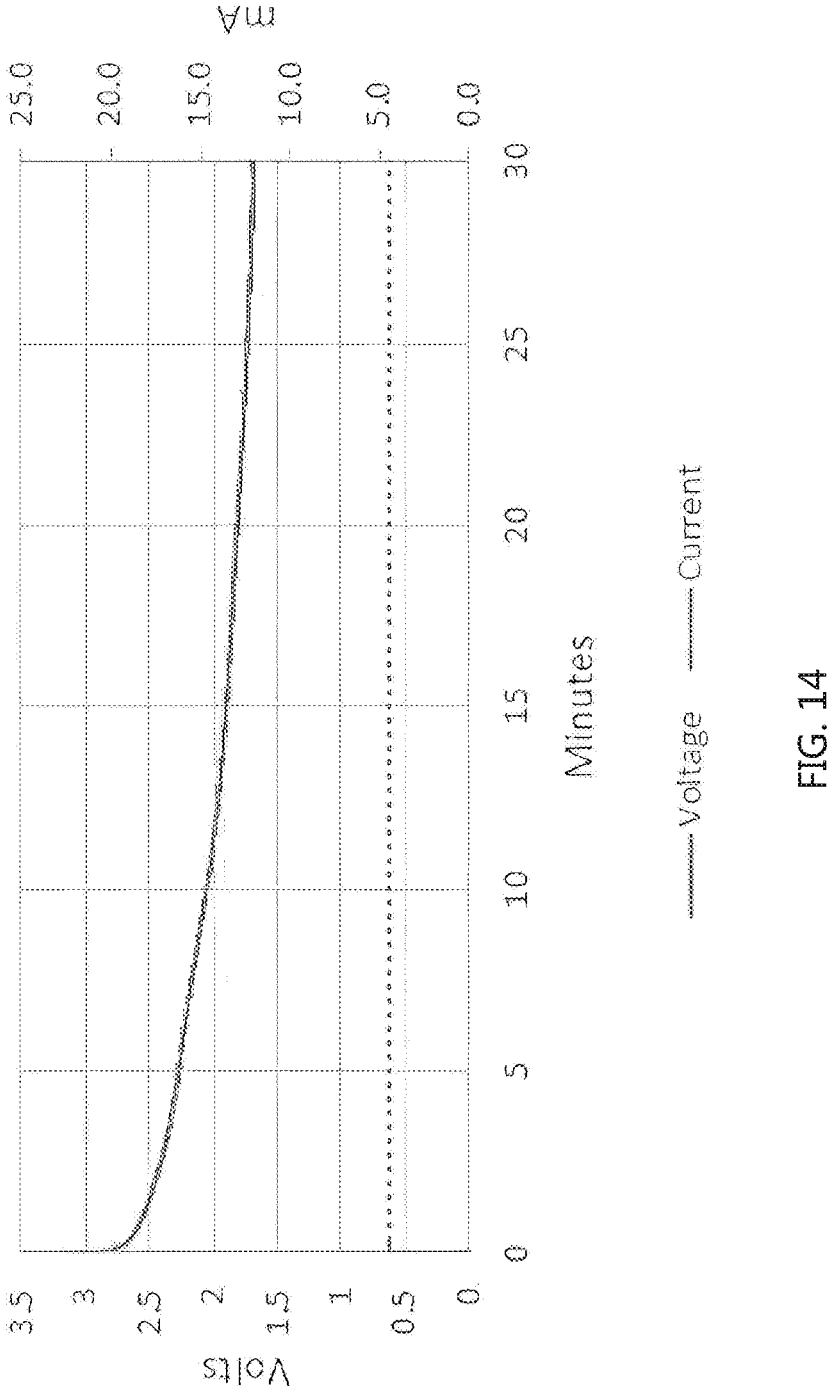

FIG. 14. Panasonic lithium cell battery (CR1220) discharge curve (solid line) at 5 mA draw (dotted line-device power consumption rate) indicates that the device is sufficiently powered beyond the 10-minute expected usage time.

Figure 15:
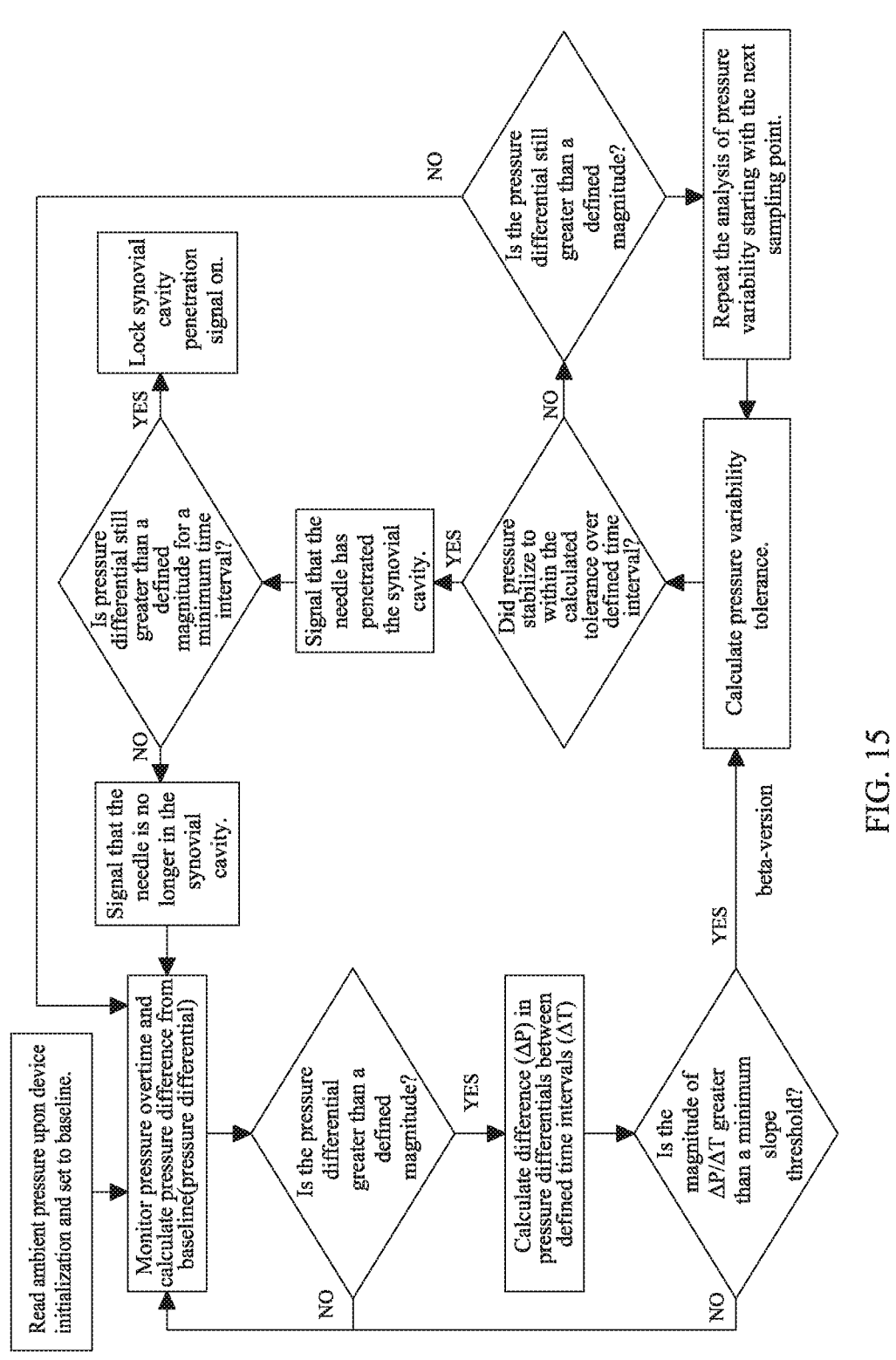

FIG. 15. Graphical representation of the beta-algorithm method deployed of this invention.

Figure 16:
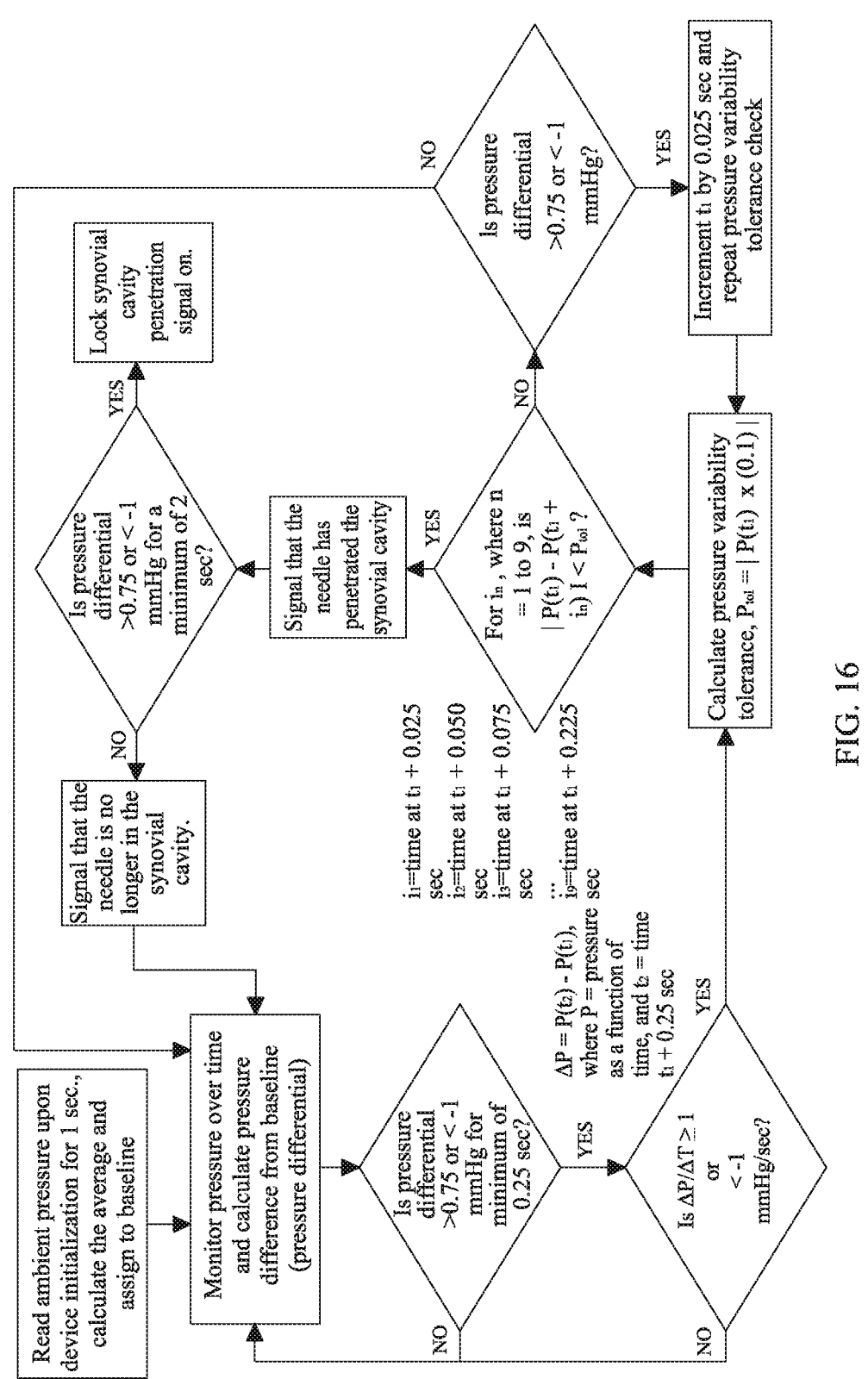

FIG. 16. Graphical representation of the beta-algorithm method deployed in this invention, with the parameters specific to Example 8 defined.

Figure 17:
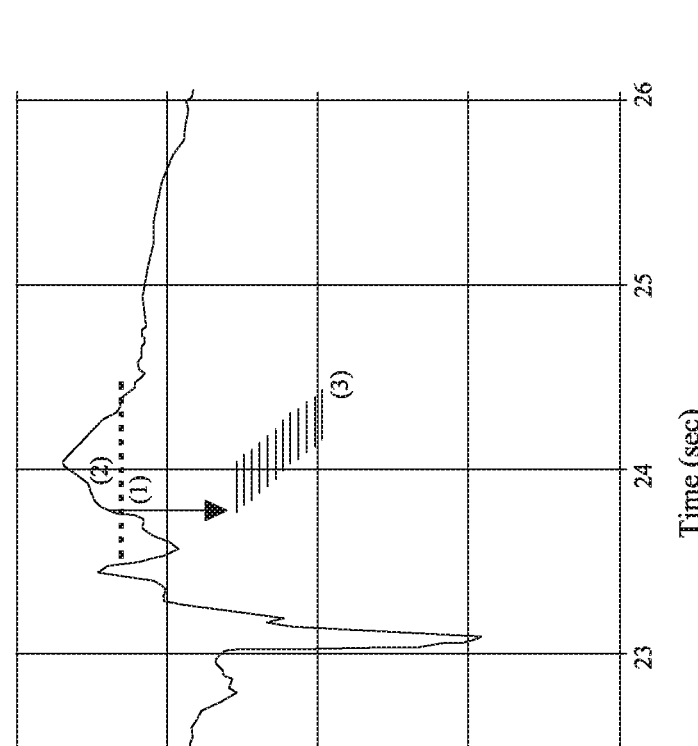

FIG. 17. Standalone device pressure over time data from extra-articular needle placement with repositioning motions by the user. Various steps are illustrated in the beta-algorithm that prevent green LED intra-articular signaling. Specifically, while the (1) ambient and (2) slope thresholds pass their minimum benchmarks, i.e. pressure<−1 mmHg and $|\Delta P/\Delta T|$>1 mmHg/sec, respectively, the stability check criteria (3), also executed over a sliding 250 ms window, is not satisfied. See Example 8 and FIG. 16 for Beta-algorithm design specifics. The dotted line equals ambient pressure threshold. The horizontal hashes equal a sliding 250 ms window in which a pressure variability tolerance check is performed.

Figure 18:
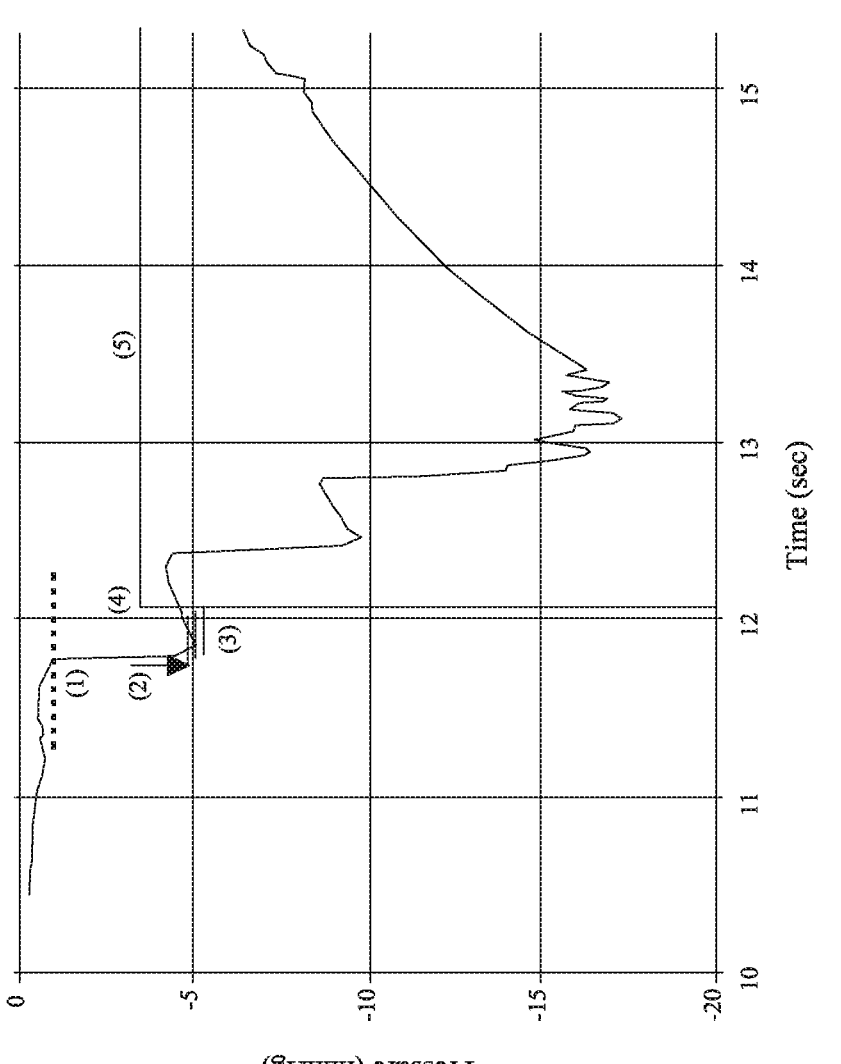

FIG. 18. Standalone device pressure over time data from ultrasound confirmed intra-articular needle placement. Various steps are illustrated in the beta-algorithm method that result in green LED intra-articular signaling. Specifically, the (1) ambient and (2) slope thresholds pass their respective minimum benchmarks, as does the stability check criteria (3). Then the device (4) communicate intraarticular needle placement by turning on the green LED. After two seconds of pressure beyond the ambient pressure thresholds, (5) the green LED activation remains in the locked on position. See Example 8 and FIG. 16 for Beta-algorithm design. The dotted line equals ambient pressure threshold. The horizontal hashes equal a sliding 250 ms windows in which a pressure variability tolerance check is performed.

Figure 19:
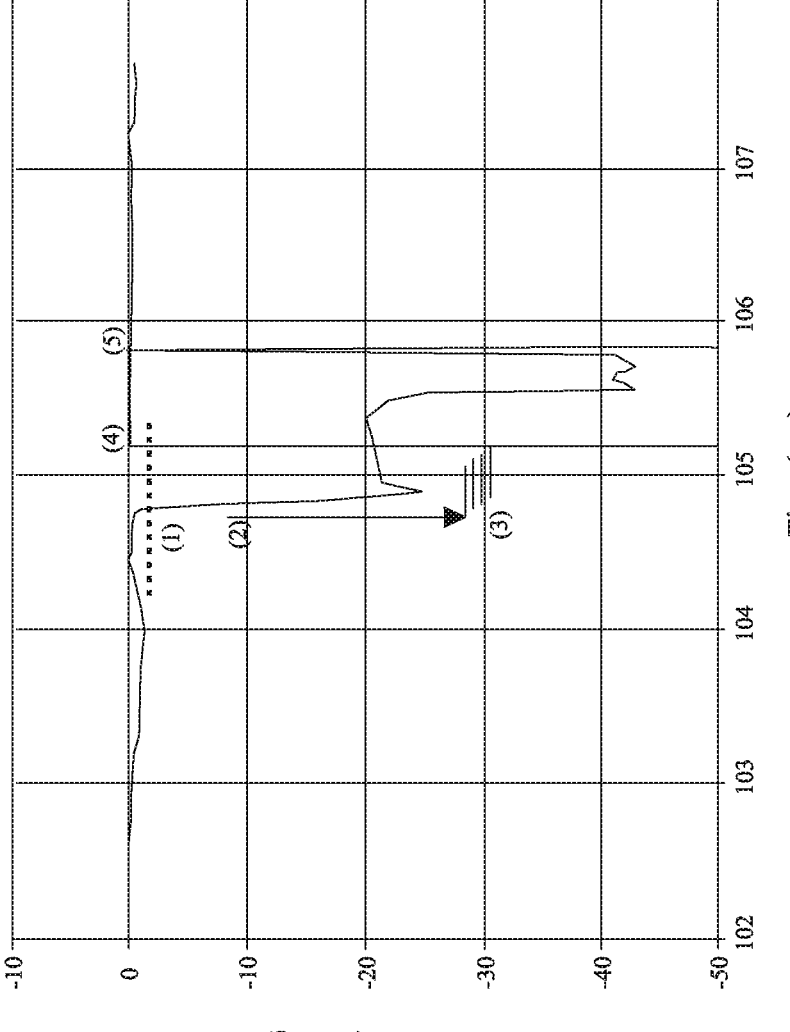

FIG. 19. Standalone device pressure over time data illustrating needle placement that is suspected of moving into and then out of the synovial cavity. Ultrasound confirmation is not performed because the green LED turned off when pressure sensed by the device returns back to ambient pressure (extraarticular pressure) prior to meeting the two-second activation "lock" window. Specifically, the (1) ambient and (2) slope thresholds pass their respective minimum benchmarks, as does the stability check criteria (3). Then the device (4) communicates intraarticular needle placement by turning on the green LED. However, (5) the device returns to ambient pressure conditions within two seconds of activation, and consequently turns off its intraarticular communication state (green LED off). See Example 8 and FIG. 16 for Beta-algorithm design. The dotted line equals ambient pressure threshold. The horizonal hashes equal a sliding 250 ms window in which a pressure variability tolerance check is performed.

DETAILED DESCRIPTION OF THE INVENTION

The target users of this device are licensed healthcare practitioners with a need to verify synovial cavity needle placement in either veterinary or human healthcare applications. An example of its use is to confirm synovial cavity needle placement prior to administering a therapeutic agent or medicament. Examples of such medicaments include but is not limited to hyaluronic acid, corticosteroids, anesthetics, antibiotics, platelet rich plasma (PRP), and mesenchymal stem cells (MSC).

Briefly, using sterile technique, the healthcare professional removes the device from its sterile packaging and attaches a therapeutic filled syringe to one end and a sterile needle to the opposing end. Then the operator powers the device (either a pull tab or a button) and observing the power-on LED, proceeds with needle insertion without priming the needle. Upon intra-articular cavity (synovial cavity) penetration, the algorithm internal to the device recognizes a pattern indicative of cavity penetration and powers a second LED, clearly signaling to the operator that they have penetrated the synovial cavity. The operator then injects a therapeutic agent or medicament into the joint cavity and withdraws the needle. The second LED mode, once triggered, remains on continuously until the self-contained battery is depleted of all power, thus ensuring that the device remains single-use. This latter point is extremely important to reducing the risk of nosocomial infection associated with multi-use medical device products.

The device of the present invention is about to 47 mm in length, 10 to 30 mm in width, 10 to 30 mm tall (with addendum of luer locks). Length is about 10 to 30 mm not including luer locks. These dimensions are illustrated in FIG. 1. Features common to all embodiments of the invention are a power source, a power source isolation mechanism, a microprocessor, male and female luer locks for secure needle and syringe attachment (constructed to ISO 594 and ISO 80369-7 specifications), a user communications mechanism, a channel (i) connecting the interior of the syringe with the lumen of the needle and (ii) exposing the pressure transducer to pressures encountered by the needle.

Unlike the device and method of U.S. Pat. No. 8,608,665, the present device records positive (supra-atmospheric) and negative (sub-atmospheric) joint pressures. The ability to detect supra-pressures confers the ability to confirm synovial cavity needle placement in positively pressured synovial joints. Positive pressure can occur in response to joint flexion, application of pressure proximal but external to the joint, and load bearing, such as standing. Joint effusions also present positive joint pressures. Accordingly, the ability to detect both positive and negative joint pressures enables the present invention to more reliably identify synovial cavities, in a wider set of circumstances. The positive joint pressure recorded and presented by the device can also be combined with other clinical characteristics to support diagnoses of effusion.

In one embodiment of the present invention, a translucent 3D stereolithographic housing is printed (Formlabs resin FLGPCL04). The housing contains a hollow tube connecting male and female luer locks positioned on opposing ends (the flow path). Within the 3D printed housing is a custom printed circuit board (PCB) on which are mounted several components: (i) low-voltage microcontroller with 8 Kb of flash memory, 1.5 Kb of SRAM, and 16 MHz processing speed (ST Microelectronics; part number STM8L101), and (ii) two LEDs for user communications (Everlight Electronics), where one LED is blue (part number EAST16084BB0) for indicating device "on" and the other LED is green (part number EAST0603GA0) for indicating joint cavity penetration, and (iii) necessary capacitors and resistors for storing and regulating power. Mounted within a hollow tube that bisects the flow path is a piezoresistive pressure sensor manufactured by Bosch (part number BMP280), which is exposed to pressures encountered within the lumen of the needle. Note that power is supplied by off the shelf 3V lithium-manganese dioxide cell batteries such as Energizer (EBR1225) or Panasonic (CR1220).

Example 1: Bench Top Device Test

A translucent housing contains a hollow tube connecting male and female luer locks positioned on opposing ends (see FIG. 2). Sealed within the housing is a circuit-board mounted piezoresistive pressure sensor, manufactured by Bosch (BMP280), and another pressures sensor manufactured by ST LPS22HB. Also, a TDK ICP-1011 Pressure Transducer is used in the present invention as the pressure transducer. When using this pressure transducer, linear voltage regulators are used. Pressure sensors are exposed to the flow path by another bisecting hollow tube approximately 2 mm in length. Also sealed within the housing are associated electronics for laptop USB supplied power and a communications control board. Data is sent to a laptop running a custom application for real-time display of pressure and time data. Following data collection, data is saved to a comma delimited text file. A diagrammatic representation of the laptop connected device and associated components are illustrated in FIG. 3. The bench top tests simulates a liquid filled pressurized joint capsule in the following manner: a 10 mL glass vial is filled with 5 mL of $H_2O$. A cap with synthetic self-sealing septum is attached to the glass vial. A manometer (Extech model 406800) is connected to a 20-gauge needle via a disposable medical grade silicone tubing. The manometer is equilibrated to ambient pressure and its needle inserted through the membrane into the air portion of the vial. A second needle is inserted into the vial, and either air is added to pressurize the vial (e.g. to 5 mmHg) or air is removed to create a vacuum (e.g. to 5 mmHg). Then both the manometer needle, and empty syringe needle are removed. Following this preparation, the vial is inverted such that liquid is now on top of the membrane. The pressure sensing device is assembled as shown in FIG. 3, whereby a 20-gauge needle and 5 mL syringe are attached. Then the device is initialized by plugging it into the USB port of the laptop and starting the data collection application. After initialization, the pressure sensors are automatically calibrated to ambient pressure. Shortly after starting data collection, the device connected needle is inserted into the liquid portion of the inverted pre-pressurized vial. This setup is illustrated in FIG. 4.

Collected data from bench testing is plotted as pressure vs time. As shown by representative data in FIG. 5, the laptop connected device detects pressures resembling known intra-articular pressures of non-effused and effused non-weight bearing human knees. Non-effused knees have reported pressures approximately spanning −5 to 10 mmHg (Alexander et al., 1996; Wood et al., 1988), and effused knees have reported pressures approximately spanning 6 to 35 mmHg (Caughey and Bywaters, 1963).

Note that the physiologic pressures observed in intra-articular joints are well within the advertised pressure detection range specifications of the bmp280 Bosch pressure sensor. With regard to pressure sampling rate capabilities consider that at relatively fast synovial cavity needle insertion speeds (2 seconds from surface tissue puncture to synovial cavity penetration), and an approximate 25 to 38 mm puncture depth, a 25 ms pressure sampling rate setting will enable the bmp280 Bosch pressure sensor to measure pressures approximately every 0.3 to 0.5 mm of tissue penetrated. This corresponds to approximately 80 pressure measurements prior to reaching the synovial cavity. Energy consumption is quite low at the 25 ms sampling rate, an approximate 420 µA draw is observed. Advertised specifications indicate absolute accuracy at +/−0.75 mmHg, and relative accuracy+/−0.09 mmHg. In short, the bmp280 Bosch pressure sensor is very sensitive and capable of detecting minute pressure differences on time scales suitable to the purpose of this invention.

Example 2: Equine Synovial Cavity Tests

The laptop connected device is used to probe the pressures of medial femorotibial (stifle) and metacarpophalangeal (fetlock) joint cavities of three horses. The primary aims of the study are, to acquire pressure over time data during joint tapping in a biological system, to observe clinical usage of the device, and lastly to gather user feedback. Horses are mildly sedated with xylazine and butorphanol. They are positioned squarely on all four legs with weight equally distributed. Aseptic techniques are employed throughout the procedure, e.g. Sterile gloving, repeated applications of chlorohexidine and isopropanol to injection area with scrubbing. The device is assembled as per FIG. 3, with the attachment of a sterile 20-gauge 3.5-inch needle and syringe. Needles are replaced after each joint tapping procedure. If it becomes apparent that liquid enters the fluid path of the device, the device is exchanged for an unused device. Pressure Profile data measured with the laptop connected device is sent to the laptop and recorded. Ultrasound guidance is employed throughout the procedure to confirm joint cavity penetration. To prevent joint contamination the device is not used to aspirate or to inject any liquid.

Ten pressure profiles are collected with the laptop connected device consisting of four fetlocks and six stifles. All fetlocks give positive pressure readings as do three of the stifles. The remaining three stifles produce negative pressure readings.

Illustrated in FIG. 6, are negative and positive pressure profiles of an equine stifle joint (upper panel) and equine fetlock joint (lower panel), as measured with the laptop connected device.

Example 3: Goat Intra-Articular Test

The laptop connected device is used to probe the intra-articular pressures of radiocarpal joints and goat stifles (femorotibial joint) from seven goats. The primary aims of the study are to acquire pressure over time data during joint tapping in a biological system, to observe clinical usage of the device, and lastly to gather user feedback. Animals are weighed, and anesthetized, and endotracheal tubes inserted to ensure airway maintenance. Blood pressure, end tidal $CO_2$, and pulse oximetry, are used throughout the procedure to monitor the animal's condition and adjust anesthesia. Each injection site is cleaned and draped in sterile fashion. Sterile technique is employed throughout the procedure. Approximately 1-3 mL of 0.25% Marcaine solution is injected subcutaneously proximal to each joint to prevent any possible pain. The device is assembled as per FIG. 3, with the attachment of sterile 21-gauge needles and syringes. Joints are then tapped, and the pressure profiles recorded with the laptop connected device. Needles are replaced after each joint tapping procedure.

Data is successfully collected on 11 radio carpal joints and 11 femorotibial joints. Radiocarpal joints and femorotibial joints exhibit both positive and negative pressure ranges. Shown in FIG. 7 are negative pressure profiles from goat radiocarpal and stifle joint taps.

Example 4: Cadaver Feasibility Studies

Two mid-femur to mid-tibial knee specimens from cadavers are obtained from donors within 48 hours post-mortem. A right knee from a 63-year old male donor, and a left knee from an 89-year old female donor are provided. Parameters that affect intra-articular pressures are controlled, such as approach portal of the needle (lateral retropatellar during ultrasound or lateral parapatellar during fluoroscopy), guidance methodology for confirming joint cavity penetration (ultrasound or fluoroscopy), flexion angle of the joint (50 degrees from fully extended during ultrasound or acute flexion during fluoroscopy), pre-procedure flexion cycles (none), patellar manipulation (none). The primary aims of the study are to acquire pressure over time data during joint tapping in a human biological system, to observe clinical usage of the device, and to gather user feedback.

The female donor's knee is placed on a holder in supine position with 50° flexion. A 21-gauge 1.5" needle is attached to the laptop connected prototype device and the device is initialized. The joint cavity is then tapped via a lateral retropatellar approach under injection guidance with a SonoSite M-Turbo ultrasound system and SonoSite L25x 13-6 MHz Linear Array Transducer. Pressure profiles collected with the device are saved to the laptop and analyzed. Shown in the upper panel of FIG. 10, is the pressure over time profile several seconds prior to and after synovial cavity penetration by the device connected needle. Also shown in the inset photo is the sonographic image that was captured when the device connected needle penetrated the joint pocket. The tip of the needle is clearly visible in the anechoic space just under and adjacent to the highly echoic patella. These sonographic anatomical landmarks are indicative of a synovial cavity needle placement.

The male donor's knee is placed on a support within the C-arm of the fluoroscopic imaging system (GE OEC 9900 Elite). The knee allowed to bend naturally under its own weight to an acute flexion angle. A 21-gauge 1.5 needle is attached to the laptop connected prototype device and the device was initialized. The joint cavity is then tapped via a lateral parapatellar approach under fluoroscopic guidance. Pressure profiles collected with the device are saved to the laptop and analyzed. Shown in the lower panel of FIG. 10, is the pressure over time profile several seconds prior to and after synovial cavity penetration by the device connected needle. Also shown in the inset photo is the fluoroscopic image that was captured when the device connected needle penetrated the joint pocket. The tip of the needle is clearly visible in the space adjacent to the lateral femoral condyle—an area surrounded by a synovial cavity.

Example 5: Alpha-Algorithm Method Design

The pressure over time data from EXAMPLE 4 is analyzed and a joint cavity penetration determination algorithm is assembled and tested. The basis for this algorithm is as follows:

1) Establish a baseline atmospheric pressure upon device initialization and set this to zero mmHg.
2) Define pressures encountered by the device above this baseline as positive or supra-atmospheric.
3) Define pressures encountered by the device that are below this baseline as negative or sub-atmospheric.
4) During needle insertion, if the magnitude of device measured pressure (either supra or sub-atmospheric pressure) is greater than 0.5 mmHg (P>[0.5 mmHg]) for 250 milliseconds (ms) or if the magnitude of the slope is greater than a pre-determined amount, then
5) at each successive time point (provided condition-4 above is maintained), calculate the difference in pressure ($\Delta\Delta P$) from the present time point to the previous time point 250 ms in the past, and
6) assigning a value of 0.250 seconds to $\Delta T$, calculate the $\Delta P/\Delta T$ slope in mmHg/second, and
7) if $\Delta P/\Delta T > 1$ mmHg/second, or if $\Delta P/\Delta T < -1$ mmHg/second, trigger the LED, LCD, or other suitable visual indication of joint penetration, and
8) optionally, display the actual pressures encountered by the device, and/or
9) optionally, indicate a warning LED, LCD, or other suitable visual or audible indication of a potential effusion when pressures encountered by the device are equal to or exceed 10 mmHg ($P \geq 10$ mmHg).

A graphical representation of the algorithm is depicted in FIG. 8. The algorithm and defined parameters specific to Example 5 are graphically depicted in FIG. 9. The algorithm correctly identifies synovial cavity penetration. The synovial cavity penetration signal is indicated by the dotted line in the upper and lower panels of FIG. 10.

In summary, the method of the invention first establishes a baseline atmospheric pressure and records a series of pressure readings at defined time intervals. Joint penetration is indicated if the difference between the reference atmospheric pressure and needle-sensed pressure is (i) beyond a defined negative or positive threshold; (ii) sustained beyond that threshold for a minimum defined period; and (iii) where the change in pressure over corresponding change time is equal to or exceeds a minimum slope criteria. Note that the slope can be either positive or negative. In the event the magnitude of the slope is greater than a predefined minimum, a tolerance value equal to the product of a factor and a pressure reading after the slope criteria is obtained. Then when if the pressure over time is less than a calculated variability tolerance over time for a predetermined same period then the needle provides a practitioners that it has been placed within the intra-articular cavity. Thereafter, if the pressure over time is less than calculated variability tolerance over a predetermined time period, the device informs the practitioner that the needle has been placed within the intra-articular cavity.

The method of the invention to administer a medicament requires attaching a syringe and needle to the device and powering on the device prior to usage. Then the user will monitor visual indicators displayed on the device during a synovial injection procedure. Upon observing the joint penetration signal, the user administers the medicament.

The method of the invention to support effusion diagnoses involves the same method as above, accept that upon observing a warning signal indicative of excessive synovial joint pressure, appropriate medical action to relieve or further diagnose the effusion is undertaken.

Example 6: Construction and Testing of Standalone Device

A translucent 3D stereolithographic housing is designed (Formlabs resin FLGPCL04). The housing contains a hollow tube connecting male and female luer locks positioned on opposing ends (see FIGS. 11 and 12). Within the 3D printed housing is a custom printed circuit board (PCB) on which are mounted several components: (i) low-voltage microcontroller with 8 Kb of flash memory, 1.5 Kb of SRAM, and 16 MHz processing speed (ST Microelectronics; STM8L101), and (ii) two LEDs for user communications (Everlight Electronics), where one LED is blue (EAST16084BB0) for indicating device "on" and the other LED is green (EAST0603GA0) for indicating joint cavity penetration, and (iii) necessary capacitors and resistors for storing and regulating power. Mounted within a hollow tube that bisects the how path is a piezoresistive pressure sensor (Bosch; BMP280). As indicated in the right panel of FIG. 12, this short hollow tube is positioned under the PCB and microcontroller. Its function is to expose the pressure sensor to the pressures encountered by the needle. Note that the power is supplied by off the shelf 3V lithium-manganese dioxide cell batteries such as Energizer (EBR1225) or Panasonic (CR1220).

Using the bench testing apparatus described in Example 1, the device is subjected to pressures>0.5 mmHg in magnitude. As illustrated in FIG. 13, the blue LED is illuminated upon powering the device, then following needle exposure to vial pressures>0.5 mmHg in magnitude, the blue LED turns off and the green "synovial penetration" LED turns on, as per expectations.

The Bosch pressures sensor, microcontroller and LEDs are collectively not expected to draw more than 5 mA. As shown in FIG. 14, the 1220 lithium cell provides adequate power beyond 30 minutes. Note that device usage is expected within 10 minutes of powering the device. A blinking mode may be implemented post 10 minutes of operation to warn the user that the device is beyond its intended operational timeframe. Preliminary feedback is that the device is of a size and weight that will not impede the performance of knee joint injections. Secondly, the luminosity and color of the current LED is readily discernable from all angles.

The above and below examples are provided as illustrative of the present invention device and methods and are not limitative thereof.

Example 7: Expanded Cadaver Studies

Five mid-femur to mid-tibial knee specimens with two week average post mortem intervals are obtained from donors (four male and one female). Lateral retropatellar intraarticular access ports are employed throughout the study, as are intra-articular needle placement confirmations by ultrasound. Knees are placed on stands with 50 degrees of flexion from the fully extended position. The primary aim of the study is to acquire pressure over time data during (i) intra-articular needle placement, and (ii) extra-articular needle placement with (a) needle repositioning and (b) with needle extraction. Then this data is used to define the beta-algorithm.

Donor's knees are placed on a holder in the supine position with 50° flexion. A 21-gauge 1.5" needle is attached to either a standalone prototype device, and the device is initialized. The joint cavity is then tapped via a lateral retropatellar approach and needle placement location (extra-articular or intra-articular) is confirmed with a SonoSite M-Turbo ultrasound system and SonoSite L25x 13-6 MHz Linear Array Transducer, Needle placement position (extraarticular vs intraarticular, and true positive vs false positives) are recorded by an observer. Pressure over time data collected on the device are later transferred to a laptop. The pressure profile data is used as an input into a virtual device running the same software as the device firmware with one exception—various algorithmic parameters are modified on the virtual device such that the positive predictive values for intraarticular signaling are improved. This approach to algorithm refinement enhances the positive predictive value.

The algorithm stemming from these efforts is described in EXAMPLE 8 and FIGS. 14 and 15.

Example 8: Beta-Algorithm Method Design

The pressure over time data from EXAMPLE 7 is analyzed, and a second-generation joint cavity penetration determination algorithm is implemented (beta-algorithm). In this example cadaveric knee data is fed into a virtual device, and the results are graphically depicted. Examples of algorithm performance are dissected and depicted in FIGS. 17 through 19. The beta-algorithm is described in FIGS. 15 and 16. The basis for this algorithm is as follows:
    1) Establish a baseline atmospheric pressure upon device initialization and set this to zero mmHg.

2) Define pressures encountered by the device above this baseline as positive or supra-atmospheric.

3) Define pressures encountered by the device that are below this baseline as negative or sub-atmospheric.

4) During needle insertion, if the device measured pressure is greater than 0.75 mmHg (P>0.75 Hg) (ms), or less than −1.0 mmHg (P<−1.0 mmHg), then 5) at each successive time point calculate the difference in pressure (ΔP) from the instant time point to the previous time point 250 ms in the past, and 6) assigning a value of 0.250 seconds to ΔT, calculate the ΔP/ΔT slope in mmHg/second.

7) If ΔP/ΔT>1 mmHg/second, or if ΔP/ΔT<−1 mmHg/second, 8) calculate pressure variability tolerance ($P_{tol}$), defined as the absolute value of 10% of the pressure at the time in which the slope criteria was satisfied ($t_1$), and 9) confirm that the next nine time points, each separated by an interval of 0.025 seconds, are correlated with pressures not exceeding $P_{tol}$ in magnitude, and 10) if any of the nine time points e correlated with pressure exceeding the ($P_{tol}$), then 11) increment $t_1$ by 0.025 see and assign $P_{tol}$ as equivalent to 10% of the pressure at the newly incremented $t_1$.

12) repeat steps 9 and 11 until nine consecutive time points correspond with pressures that fall within the $P_{tol}$, and satisfying this condition, 12) trigger a LED, LCD, or other suitable visual indication of joint penetration, and 13) optionally, the visual indicator of joint penetration is locked in the "on" state if after two seconds, pressures remain outside of the ambient pressure thresholds, or failing this, return to step-4.

14) Optionally, the actual pressures encountered by the device are displayed, and/or optionally, indicate a warning LED, LCD, or other suitable visual or audible indication of a potential effusion when pressures encountered by the device are equal to or exceed 10 mmHg (P≥10 mmHg).

BIBLIOGRAPHY

Alexander, C., Caughey, D., Withy, S., Van Puymbroeck, E., and Munoz, D. (1996). Relation between flexion angle and intraarticular pressure during active and passive movement of the normal knee. J Rheumatol 23, 889-895.

Berkoff, D. J., Miller, L. E., and Block, J. E. (2012). Clinical utility of ultrasound guidance for intra-articular knee injections: a review. Clin Interv Aging 7, 89-95.

Caughey, D. E., and Bywaters, E. G. (1963). Joint fluid pressure in chronic knee effusions. Ann. Rheum. Dis. 22, 106-109.

Douglas, R. J. (2014). Aspiration and injection of the knee joint: approach portal. Knee Surg Relat Res 26, 1-6.

Finnoff, J. T., Hall, M. M., Adams, E., Berkoff, D., Concoff, A. L., Dexter, W., and Smith, J. (2015). American Medical Society for Sports Medicine (AMSSM) position statement: interventional musculoskeletal ultrasound in sports medicine. Br J Sports Med 49, 145-150.

Goddard, N., and Gosling, P. (1988). Intra-articular fluid pressure and pain in osteoarthritis of the hip. The Journal of Bone and Joint Surgery. British Volume 70-B, 52-55.

Hauzeur, J. P., Mathy, L., and De Maertelaer, V. (1999). Comparison between clinical evaluation and ultrasonography in detecting hydrarthrosis of the knee. J. Rheumatol. 26, 2681-2683.

Hermans, J., Bierma-Zeinstra, S. M. A., Bos, P. K., Verhaar, J. A. N., and Reijman, M. (2011). The most accurate approach for intra-articular needle placement in the knee joint: a systematic review. Semin Arthritis Rheum 41, 106-115.

Hill, C. L., Gale, D. G., Chaisson, C. E., Skinner, K., Kazis, L., Gale, M. E., and Felson, D. T. (2001). Knee effusions, popliteal cysts, and synovial thickening: association with knee pain in osteoarthritis. J Rheumatol 28, 1330-1337.

Irvin, W. O. (2015). Concepts of Etiologies and Effects of Normal Human Knee Pressure Variations. Anat Physiol 5, 172.

Jones, A., Regan, M., Ledingham, J., Pattrick, M., Manhire, A., and Doherty, M. (1993). Importance of placement of intra-articular steroid injections. BMJ 307, 1329-1330.

Kane, D., Balint, P. V., and Sturrock, R. D. (2003). Ultrasonography is superior to clinical examination in the detection and localization of knee joint effusion in rheumatoid arthritis. The Journal of Rheumatology 30, 966-971.

Landstrom, Sytsma, T. T., and Greenland, L. S. (2020). Rethinking Viscosupplementation: Ultrasound-Versus Landmark-Guided Injection for. Knee Osteoarthritis. Journal of Ultrasound in Medicine 39, 113-117.

Maricar, N., Callaghan, M. J., Parkes, M. J., Felson, D. T., and O'Neill, T. W. (2016). Clinical assessment of effusion in knee osteoarthritis-A systematic review. Semin Arthritis Rheum 45, 556-563.

Sibbitt, Peisajovich, A., Michael, A. A., Park, K. S., Sibbitt, R. R., Band, P. A., and Bankhurst, A. D. (2009). Does sonographic needle guidance affect the clinical outcome of intraarticular injections? J Rheumatol 36, 1892-1902.

Strand, E., Martin, G. S., Crawford, M. P., Kamerling, S. G., and Burba, D. J. (1998). Intra-articular pressure, elastance and range of motion in healthy and injured racehorse metacarpophalangeal joints. Equine Veterinary Journal 30, 520-527.

Telikicherla, M., and Kamath, S. U. (2016). Accuracy of Needle Placement into the Intra-Articular Space of the Knee in Osteoarthritis Patients for Viscosupplementation. J Clint Diagn Res 10, RC15-RC17.

Wood, L., Ferrell, W. R., and Baxendale, R. H. (1988). Pressures in normal and acutely distended human knee joints and effects on quadriceps maximal voluntary contractions. Q J Exp Physiol 73, 305-314.

What is claimed is:

1. A device for synovial cavity injections, said device comprising:

a. a power source;

b. a non-conductive pull-tab or power isolator;

c. a pressure transducer;

d. a microprocessor;

e. male and female luer locks; and f. a path connecting a syringe to a needle;

wherein the microprocessor is configured to:

measure and record pressure changes at predefined time intervals, responsive to determining that pressure is positive, greater than 0.5 mmHg, and exceeds previously defined thresholds for a predefined time period, calculate a change in pressure over change in time slope between two time points, and responsive to determining that a magnitude of the slope is greater than a predefined minimum and that a stability check criteria is satisfied, generate a signal to confirm that the needle has been placed within the synovial cavity.

2. The device of claim 1, additionally comprising: one or more light emitting diodes of different colors that illuminate when the needle connected to the device is exposed to the synovial cavity.

3. The device of claim 1, wherein said device has dimensions of about 27 to about 47 mm in length, about 10 to about 30 mm height and about 10 to about 30 mm width.

4. The device of claim 3, said device further comprising: a pressure sensor configured to read and share pressure readings in real time.

5. The device of claim 4, wherein the device is used in the synovial cavity of a human being.

6. The device of claim 5, wherein the synovial cavity is found within a knee, hip, shoulder, or spine.

7. The device of claim 1, wherein the pressure changes comprise biological tissue pressure, and/or biological cavity pressure measurements obtained over time.

8. The device of claim 3, wherein the power source is a lithium-manganese dioxide cell battery.

9. The device of claim 3, wherein the pressure transducer is a piezoresistive pressure sensor.

10. The device of claim 3, wherein the microprocessor is a low-voltage microcontroller with flash memory, static random access memory, and processor.

\* \* \* \* \*